(12) United States Patent
Li et al.

(10) Patent No.: US 6,262,107 B1
(45) Date of Patent: *Jul. 17, 2001

(54) WATER SOLUBLE PACLITAXEL PRODRUGS

(75) Inventors: Chun Li, Missouri City; Sidney Wallace; Dong-Fang Yu, both of Houston; David J. Yang, Sugar Land, all of TX (US)

(73) Assignee: PG-TXL Company L.P., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/346,263

(22) Filed: Jul. 1, 1999

Related U.S. Application Data

(63) Continuation of application No. 08/815,104, filed on Mar. 11, 1997, now Pat. No. 5,977,163.
(60) Provisional application No. 60/013,184, filed on Mar. 12, 1996.

(51) Int. Cl.⁷ .................... A01N 43/02; C07D 305/00; A61K 51/04; A61B 5/055
(52) U.S. Cl. .................... 514/449; 549/510; 549/511; 424/1.65; 424/9.36
(58) Field of Search .................... 514/449; 549/510, 549/511; 527/200; 546/196; 548/525; 424/1.65

(56) References Cited

U.S. PATENT DOCUMENTS

| | | |
|---|---|---|
| 4,356,166 | 10/1982 | Peterson et al. . |
| 4,942,184 | 7/1990 | Haugwitz et al. ............. 514/449 |
| 4,960,790 | 10/1990 | Stella et al. ............. 514/449 |
| 5,059,699 | 10/1991 | Kingston et al. ............. 549/511 |
| 5,087,616 | 2/1992 | Myers et al. ............. 514/21 |
| 5,380,751 | 1/1995 | Chen et al. ............. 514/449 |
| 5,422,364 | 6/1995 | Nicolaou et al. ............. 514/449 |
| 5,468,769 | 11/1995 | Klein et al. ............. 514/449 |
| 5,473,055 | 12/1995 | Mongelli et al. ............. 530/329 |
| 5,489,589 | 2/1996 | Wittman et al. ............. 514/232 |
| 5,621,001 | 4/1997 | Canetta et al. ............. 514/449 |
| 5,641,803 | 6/1997 | Carretta et al. ............. 514/449 |
| 5,716,981 | 2/1998 | Hunter et al. . |
| 5,733,925 | 3/1998 | Kunz et al. . |
| 5,762,909 | 6/1998 | Uzgiris ............. 424/9.34 |
| 5,811,447 | 9/1998 | Kunz et al. . |
| 5,873,904 | 2/1999 | Ragheb et al. . |
| 5,880,131 | 3/1999 | Greenwald et al. ............. 514/279 |
| 5,886,026 | 3/1999 | Hunter et al. . |
| 5,981,568 | 11/1999 | Kunz et al. . |
| 6,005,020 | 12/1999 | Loomis . |
| 6,028,164 | 2/2000 | Loomis . |

FOREIGN PATENT DOCUMENTS

| | | | |
|---|---|---|---|
| 0558959 | 9/1993 | (EP) | ............. C07D/305/14 |
| 0569281 | 11/1993 | (EP) | ............. C07D/305/14 |
| 0604910 | 7/1994 | (EP) | ............. C07F/9/655 |
| 5286868 | 11/1993 | (JP) . | |

OTHER PUBLICATIONS

Zunino et al., "Anti–tumor activity of daunorubicin linked to poly–L–aspartic acid," *Int. J. Cancer.* 30:465, 1982.

Pratesi et al., "Poly–L–aspartic acid as a carrier for doxorubicin: a comparative in vivo study of free and polymer–bound drug," *Br. J. Cancer.* 52:841–848, 1985.

*Primary Examiner*—Michael G. Hartley
(74) *Attorney, Agent, or Firm*—Foley & Lardner

(57) ABSTRACT

Disclosed are water soluble compositions of paclitaxel and docetaxel formed by conjugating the paclitaxel or docetaxel to a water soluble chelator, polyethylene glycol or polymer such as poly(1-glutamic acid) or poly(1-aspartic acid). Also disclosed are methods of using the compositions for treatment of tumors, auto-immune disorders such as rheumatoid arthritis and for prediction of paclitaxel uptake by tumors and radiolabeled DTPA-paclitaxel tumor imaging. Other embodiments include the coating of implantable stents for prevention of restenosis.

16 Claims, 11 Drawing Sheets

FIG. 1A
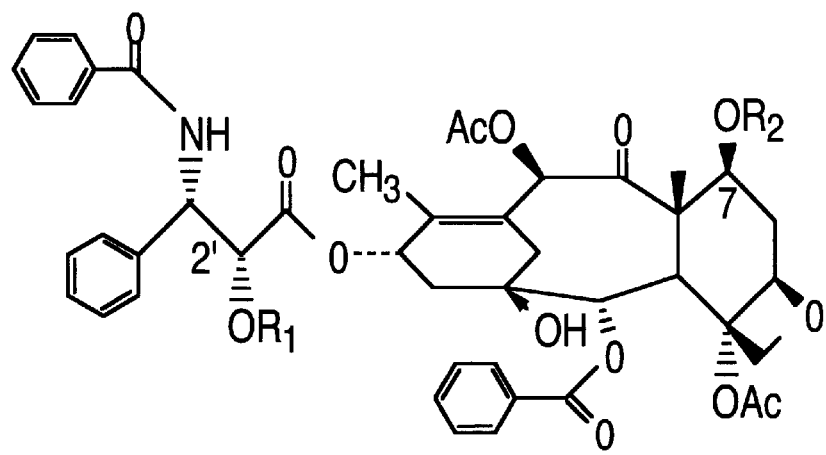
Paclitaxel: R1 = R2 = H
PEG - Paclitaxel:
    R1= -COCH$_2$CH$_2$CONHCH$_2$CH$_2$(OCH$_2$CH$_2$)$_n$OCH$_3$
    R2 = H
7 - DTPA - paclitaxel:
    R1 = H
    R2 =
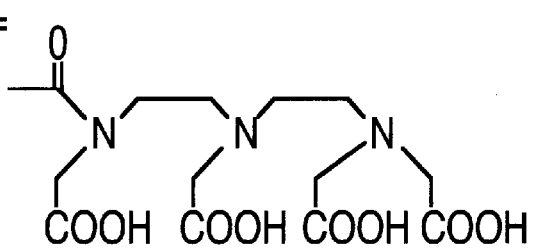
2' - DTPA - paclitaxel:
    R1 =              R2 = H
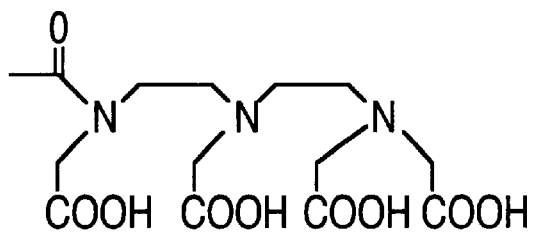

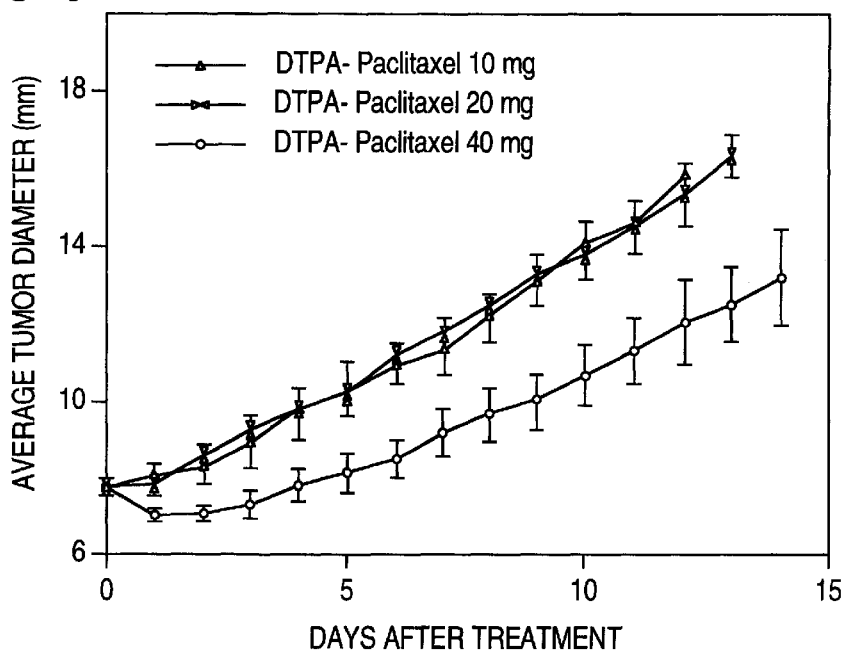
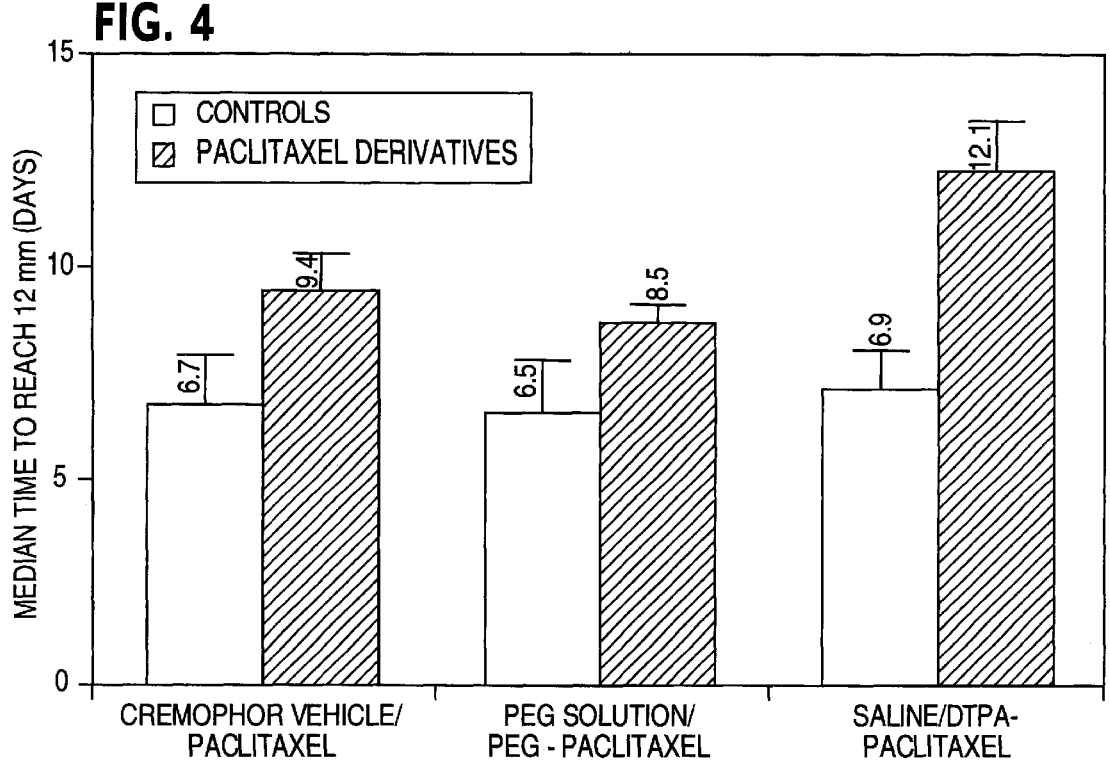

WATER SOLUBLE PACLITAXEL PRODRUGS

RELATED APPLICATIONS

This application is a continuation of application Ser. No. 08/815,104, filed Mar. 11, 1997, U.S. Pat. No. 5,977,163, which claims priority to U.S. Provisional Application No. 60/013,184, filed Mar. 12, 1996. The disclosures of the aforementioned applications are incorporated herein by reference in their entirety.

FIELD OF THE INVENTION

The present invention relates generally to the fields of pharmaceutical compositions to be used in the treatment of cancer, autoimmune diseases and restenosis. The present invention also relates to the field of pharmaceutical preparations of anticancer agents such as paclitaxel (Taxol) and doectaxel (Taxotere), in particular making paclitaxel water soluble by conjugating the drug to water soluble moieties.

BACKGROUND OF THE INVENTION

Paclitaxel, an anti-microtubule agent extracted from the needles and bark of the Pacific yew tree, *Taxus brevifolia*, has shown a remarkable anti-neoplastic effect in human cancer in Phase I studies and early Phase II and III trials (Horwitz et al., 1993). This has been reported primarily in advanced ovarian and breast cancer. Significant activity has been documented in small-cell and non-small cell lung cancer, head and neck cancers, and in metastatic melanoma. However, a major difficulty in the development of paclitaxel for clinical trial use has been its insolubility in water.

Docetaxel is semisynthetically produced from 10-deacetyl baccatin III, a noncytotoxic precursor extracted from the needles of Taxus baccata and esterified with a chemically synthesized side chain (Cortes and Pazdur, 1995). Various cancer cell lines, including breast, lung, ovarian, and colorectal cancers and melanomas have been shown to be responsive to docetaxel. In clinical trials, docetaxel has been used to achieve complete or partial responses in breast, ovarian, head and neck cancers, and malignant melanoma.

Paclitaxel is typically formulated as a concentrated solution containing paclitaxel 6 mg per milliliter of Cremophor EL (polyoxyethylated castor oil) and dehydrated alcohol (50% v/v) and must be further diluted before administration (Goldspiel, 1994). The amount of Cremophor EL necessary to deliver the required doses of paclitaxel is significantly higher than that administered with any other drug that is formulated in Cremophor. Several toxic effects have been attributed to Cremophor, including vasodilation, dyspnea, and hypotension. This vehicle has also been shown to cause serious hypersensitivity in laboratory animals and humans (Weiss et al., 1990). In fact, the maximum dose of paclitaxel that can be administered to mice by i.v. bolus injection is dictated by the acute lethal toxicity of the Cremophor vehicle (Eiseman et al., 1994). In addition, Cremophor EL, a surfactant, is known to leach phthalate plasticizers such as di(2-ethylhexyl)phthalate (DEHP) from the polyvinylchloride bags and intravenous administration tubing. DEHP is known to cause hepatotoxicity in animals and is carcinogenic in rodents. This preparation of paclitaxel is also shown to form particulate matter over time and thus filtration is necessary during administration (Goldspiel, 1994). Therefore, special provisions are necessary for the preparation and administration of paclitaxel solutions to ensure safe drug delivery to patients, and these provisions inevitably lead to higher costs.

Prior attempts to obtain water soluble paclitaxel have included the preparation of prodrugs of paclitaxel by placing solubilizing moieties such as succinate and amino acids at the 2'-hydroxyl group or at the 7-hydroxyl position (Deutsch et al., 1989; Mathew et al., 1992). However, these prodrugs have not proven chemically stable enough for development. For example, Deutsch et al. (1989) report a 2'-succinate derivative of paclitaxel, but water solubility of the sodium salt is only about 0.1% and the triethanolamine and N-methylglucamine salts were soluble at only about 1%. In addition, amino acid esters were reported to be unstable. Similar results were reported by Mathew et al. (1992). Greenwald et al. reported the synthesis of highly water-soluble 2' and 7-polyethylene glycol esters of taxol (Greenwald et al., 1994), however, no data concerning the In vivo antitumor activity of these compounds were reported (Greenwald et al. 1995).

Others attempts to solve these problems have involved microncapsulation of paclitaxel in both liposomes and nanospheres (Bartoni and Boitard, 1990). The liposome formulation was reported to be as effective as free paclitaxel, however only liposome formulations containing less than 2% paclitaxel were physically stable (Sharma and Straubinger, 1994). Unfortunately, the nanosphere formulation proved to be toxic. There is still a need therefore for a water soluble paclitaxel formulation that can deliver effective amounts of paclitaxel and docetaxel without the disadvantages caused by the insolubility of the drug.

Another obstacle to the widespre ad use of paclitaxel is the limited resources from which paclitaxel is produced, causing paclitaxel therapy to be expensive. A course of treatment may cost several thousand dollars, for example. There is the added disadvantage that not all tumors respond to paclitaxel therapy, and this may be due to the paclitaxel not getting into the tumor. There is an immediate need, therefore, for effective formulations of paclitaxel and related drugs that are water soluble with long serum half lives for treatment of tumors, autoimmune diseases such as rheumatoid arthritis, as well as for the prevention of restenosis of vessels subject to traumas such as angioplasy and stenting.

SUMMARY OF THE INVENTION

The present invention seeks to overcome these and other drawbacks inherent in the prior art by providing compositions comprising a chemotherapeutic and antiangiogenic drug, such as paclitaxel or docetaxel conjugated to a water soluble polymer such as a polyglutamic acid or a polyaspartic acid, for example, or to a water soluble metal chelator. These compositions are shown herein to be surprisingly effective as anti-tumor agents against exemplary tumor models, and are expected to be at least as effective as pactitaxel or docetaxel against any of the diseases or conditions for which taxanes or taxoids are known to be effective. The compositions of the invention provide water soluble taxoids to overcome the drawbacks associated with the insolubility of the drugs themselves, and also provide the advantages of controlled release so that tumors are shown herein to be eradicated in animal models after a single intravenous administration.

The methods described herein could also be used to make water soluble polymer conjugates of other therapeutic agents, contrast agents and drugs, including etopside, teniposide, fludarabine, doxorubicin, daunomycin, emodin, 5-fluorouracil, FUDR, estradiol, camptothecin, retinoic acids, verapamil, epothilones and cyclosporin. In particular, those agents with a free hydroxyl group would be conjugated to the polymers by similar chemical reactions as described herein for paclitaxel. Such conjugation would be well within the skill of a routine practitioner of the chemical art, and as such would fall within the scope of the claimed invention. Those agents would include, but would not be limited to etopside, teniposide, camptothecin and the epothilones. As used herein, conjugated to a water soluble polymer means the covalent bonding of the drug to the polymer or chelator.

It is also understood that the water soluble conjugates of the present invention may be administered in conjunction with other drugs, including other anti-tumor or anti-cancer drugs. Such combinations are known in the art. The water soluble paclitaxelor docetaxel of the present invention may, in certain types of treatment, be combined with a platinum drug, an antibiotic such as doxorubicin or daunorubicin, for example, or other drugs that are used in combination with Taxol.

Conjugation of chemotherapeutic drugs to polymers is an attractive approach to reduce systemic toxicity and improve the therapeutic index. Polymers with molecular mass larger than 30 kDa do not readily diffuse through normal capillaries and glomerular endothelium, thus sparing normal tissue from irrelevant drug-mediated toxicity (Maeda and Matsumura, 1989; Reynolds, 1995). On the other hand, it is well established that malignant tumors often have disordered capillary endothelium and greater permeability than normal tissue vasculature (Maeda and Matsumura, 1989; Fidler et al., 1987). Thus, a polymer-drug conjugate that would normally remain in the vasculature may selectively leak from blood vessels into tumors, resulting in tumor accumulation of active therapeutic drug. Additionally, polymer-drug conjugates may act as drug depots for sustained release, producing prolonged drug exposure to tumor cells. Finally, water soluble polymers may be used to stabilize drugs, as well as to solubilize otherwise insoluble compounds. At present, a variety of synthetic and natural polymers have been examined for their ability to enhance tumor-specific drug delivery (Kopecek, 1990, Maeda and Matsumura, 1989). However, only a few are currently undergoing clinical evaluation, including SMANCS in Japan and HPMA-Dox in the United Kingdom (Maeda, 1991; Kopecek and Kopeckova, 1993).

In the present disclosure, a taxoid is understood to mean those compounds that include paclitaxels and docetaxel, and other chemicals that have the taxane skeleton (Cortes and Pazdur, 1995), and may be isolated from natural sources such as the Yew tree, or from cell culture, or chemically synthesized molecules, and preferred is a chemical of the general chemical formula, $C_{47}H_{51}NO_{14}$, including [2aR-[2aα,4β,4αβ,6β,9α(αR*,βS*),11α,12α,12aα,12bα,]]-β-(Benzoylamino)-α-hydroxybenzenepropanoic acid 6, 12b, bis(acetyloxy)-12-(benzoyloxy)-2a,3,4,4a,5,6,9,10,11,12, 12a,12b-dodecahydro-4,11-dihydroxy-4a,8,13,13-tetramethyl-5-oxo-7,11-methano-1H-cyclodeca[3,4]benz-[1,2-b]oxet-9-yl ester. It is understood that paclitaxel and docetaxel are each more effective than the other against certain types of tumors, and that in the practice of the present invention, those tumors that are more susceptible to a particular taxoid would be treated with that water soluble taxoid conjugate.

In those embodiments in which the paclitaxel is conjugated to a water soluble metal chelator, the composition may further comprise a chelated metal ion. The chelated metal ion of the present invention may be an ionic form of any one of aluminum, boron, calcium, chromium, cobalt, copper, dysprosium, erbium, europium, gadolinium, gallium, germanium, holmium, indium, iridium, iron, magnesium, manganese, nickel, platinum, rhenium, rubidium, ruthenium, samarium, sodium, technetium, thallium, tin, yttrium or zinc. In certain preferred embodiments, the chelated metal ion will be a radionuclide, i.e. a radioactive isotope of one of the listed metals. Preferred radionuclides include, but are not limited to $^{67}Ga$, $^{68}Ga$, $^{111}In$, $^{99m}Tc$, $^{90}Y$, $^{114m}In$ and $^{193m}Pt$.

Preferred water soluble chelators to be used in the practice of the present invention include, but are not limited to, diethylenetriaminepentaacetic acid (DTPA), ethylenediaminetetraacetic acid (EDTA), 1,4,7,10-tetraazacyclododecane-N,N',N'',N'''-tetraacetate (DOTA), tetraazacyclotetradecane-N,N',N'',N'''-tetraacetic acid (TETA), hydroxyethylidene diphosphonate (HEDP), dimercaptosuccinic acid (DMSA), diethylenetriaminetetramethylenephosphonic acid (DTTP) and 1-(p-aminobenzyl)-DTPA, 1,6-diamino hexane-N,N,N',N'-tetraacetic acid, DPDP, and ethylenebis (oxyethylenenitrilo)-tetraacetic acid, with DTPA being the most preferred. A preferred embodiment of the present invention may also be a composition comprising $^{111}In$-DTPA-paclitaxel.

In certain embodiments of the present invention, the paclitaxel or docetaxel may be conjugated to a water soluble polymer, and preferably the polymer is conjugated to the 2' or the 7-hydroxyl or both of the paclitaxel or docetaxel. Thus when functional groups are used for drug conjugation, as above with the C2'-hydroxyl of paclitaxel, a degradable linkage, in this case, an ester, is used to ensure that the active drug is released from the polymeric carrier. Preferred polymers include, but are not limited to polyethylene glycol, poly(1-glutamic acid), poly(d-glutamic acid), poly(dl-glutamic acid), poly(1-aspartic acid), poly(d-aspartic acid), poly(dl-aspartic acid), polyethylene glycol, copolymers of the above listed polyamino acids with polyethylene glycol, polycaprolactone, polyglycolic acid and polylactic acid, as well as polyacrylic acid, poly(2-hydroxyethyl1-glutamine), carboxymethyl dextran, hyaluronic acid, human serum albumin and alginic acid, with polyethylene glycol, polyaspartic acids and polyglutamic acids being particularly preferred. The polyglutamic acids or polyaspartic acids of the present invention preferably have a molecular weight of about 5,000 to about 100,000 with about 20,000 to about 80,000, or even about 30,000 to about 60,000 being more preferred.

It is understood that the compositions of the present invention may be dispersed in a pharmaceutically acceptable carrier solution as described below. Such a solution would be sterile or aseptic and may include water, buffers, isotonic agents or other ingredients known to those of skill in the art that would cause no allergic or other harmful reaction when administered to an animal or human subject. Therefore, the present invention may also be described as a pharmaceutical composition comprising a chemotherapeutic or anti-cancer drug such as paclitaxel or docetaxel conjugated to a high molecular weight water soluble polymer or to a chelator. The pharmaceutical composition may include polyethylene glycol, polyglutamatic acids polyaspartic acids or a chelator, preferably DTPA. It is also understood that a radionuclide may be used as an anti-tumor agent, or drug, and that the present pharmaceutical composition may include a therapeutic amount of a chelated radioactive isotope.

In certain embodiments, the present invention may be described as a method of determining the uptake of a chemotherapeutic drug such as paclitaxel or docetaxel by tumor tissue. This method may comprise obtaining a conjugate of the drug and a metal chelator with a chelated metal ion, contacting tumor tissue with the composition and detecting the presence of the chelated metal ion in the tumor tissue. The presence of the chelated metal ion in the tumor tissue is indicative of uptake by the tumor tissue. The chelated metal ion may be a radionuclide and the detection may be scintigraphic. The tumor tissue may also be contained in an animal or a human subject and the composition would then be administered to the subject.

The present invention may also be described in certain embodiments as a method of treating cancer in a subject. This method includes obtaining a composition comprising a chemotherapeutic drug such as paclitaxel or docetaxel conjugated to a water soluble polymer or chelator and dispersed in a pharmaceutically acceptable solution and administering the solution to the subject in an amount effective to treat the tumor. Preferred compositions comprise paclitaxel or docetaxel conjugated to a polyglutamic acids or polyaspartic acids and more preferably to poly (1-glutamic acid) or poly 1-aspartic acid). The compositions of the invention are understood to be effective against any type of cancer for which the unconjugated taxoid is shown to be effective and would include, but not be limited to breast cancer, ovarian cancer, malignant melanoma, lung cancer, gastric cancer, colon cancer, head and neck cancer or leukemia.

The method of treating a tumor may include some prediction of the paclitaxel or docetaxel uptake in the tumor prior to administering a therapeutic amount of the drug or prodrug. This method may include any of the imaging techniques discussed above in which a paclitaxel-chelator-chelated metal is administered to a subject and detected in a tumor. This step provides a cost effective way of determining that a particular tumor would not be expected to respond to DTPA-paclitaxel therapy in those cases where the drug does not get into the tumor. It is contemplated that if an imaging technique can be used to predict the response to paclitaxel and to identify patients that are not likely to respond, great expense and crucial time may be saved for the patient. The assumption is that if there is no reasonable amount of chemotherapeutic agent deposited in the tumor, the probability of tumor response to that agent is relatively small.

In certain embodiments the present invention may be described as a method of obtaining a body image of a subject. The body image is obtained by administering an effective amount of a radioactive metal ion chelated to a paclitaxel-chelator conjugate to a subject and measuring the scintigraphic signals of the radioactive metal to obtain an image.

The present invention may also be described in certain broad aspects as a method of decreasing at least one symptom of a systemic autoimmune disease comprising administering to a subject having a systemic autoimmune disease an effective amount of a composition comprising paclitaxel or docetaxel conjugated to poly-1-glutamic acid or poly-1-aspartic acid. Of particular interest in the context of the present disclosure is the treatment of rheumatoid arthritis, which is known to respond in some cases to taxol when administered in the standard Cremophor formulation (U.S. Pat. No. 5,583,153). As in the treatment of tumors, it is contemplated that the effectiveness of the water soluble taxoids of the present invention will not be diminished by the conjugation to a water soluble moiety, and that the water soluble prodiug may act as a controlled release formulation that releases the active drug over a period of time. Therefore, the compositions of the present invention are expected to be as effective as Taxol against rheumatoid arthritis, for example, but will offer the advantage a controlled release. It is also understood that the taxoid compositions of the present invention may be used in combination with other dnigs, such as an angiogenesis inhibitor (AGM-1470) (Oliver et al., 1994) or methotrexate.

The finding that paclitaxel also inhibits restenosis after balloon angioplasty indicates that the water soluble paclitaxels and docetaxels of the present invention will find a variety of applications beyond direct parenteral administration (WO 9625176). For example, it is contemplated that water soluble paclitaxel will be useful as a coating for implanted medical devices, such as tubings, shunts, catheters, artificial implants, pins, electrical implants such as pacemakers, and especially for arterial or venous stents, including balloon-expandable stents. In these embodiments it is contemplated that water soluble paclitaxel may be bound to an implantable medical device, or alternatively, the water soluble paclitaxel may be passively adsorbed to the surface of the implantable device. For example, stents may be coated with polymer-drug conjugates by dipping the stent in polymer-drug solution or spraying the stent with such a solution. Suitable materials for the implantable device should be biocompatible and nontoxic and may be chosen from the metals such as nickel-titanium alloys, steel, or biocompatible polymers, hydrogels, polyurethanes, polyethylenes, ethylenevinyl acetate copolymers, etc. In a preferred embodiment the water soluble paclitaxel, especially a PG-paclitaxel conjugate, is coated onto a stent for insertion into an artery or vein following balloon angioplasty. The invention may be described therefore, in certain broad aspects as a method of inhibiting arterial restenosis or arterial occlusion following vascular trauma comprising administering to a subject in need thereof, a composition comprising paclitaxel or docetaxel conjugated to poly-1-glutamic acid or poly-1-aspartic acid. In the practice of the method, the subject may be a coronary bypass, vascular surgery, organ transplant or coronary or arterial angioplasty patient, for example, and the composition may be administered directly, intravenously, or even coated on a stent and the stent is implanted at the sight of vascular trauma.

An embodiment of the invention is, therefore, an implantable medical device, wherein the device is coated with a composition comprising paclitaxel or docetaxel conjugated to polyglutamic acids or polyaspartic acids in an amount effective to inhibit smooth muscle cell proliferation. A preferred device is a stent coated with the compositions of the present invention as described herein, and in certain preferred embodiments, the stent is adapted to be used after balloon angioplasty and the coating is effective to inhibit restenosis.

In certain preferred embodiments, the invention may be described as a composition comprising polygiutamic acids conjugated to the 2' or 7 hydroxyl or both of paclitaxel, or even a composition comprising polyaspartic acid conjugated to the 2' or 7 hydroxyl or both of paclitaxel. As used herein, the terms "a polyglutamic acid" or "polyglutamic acids" include poly (1-glutamic acid), poly (d-glutamic acid) and poly (dl-glutamic acid) and the terms "a polyaspartic acid" or "polyaspartic acids" include poly (1-aspartic acid), poly (d-aspartic acid) and poly (dl-aspartic acid).

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

BRIEF DESCRIPTION OF THE DRAWINGS

FIG. 1A shows the chemical structure of paclitaxel, PEG-paclitaxel and DTPA-paclitaxel.

FIG. 3 shows the antitumor effect of DTPA-paclitaxel on MCa-4 mammary tumors.

FIG. 4 shows the median time (days) to reach tumor diameter of 12 mm after treatment with paclitaxel, DTPA-paclitaxel and PEG-paclitaxel.

DETAILED DESCRIPTION OF THE INVENTION

Figure 1B:
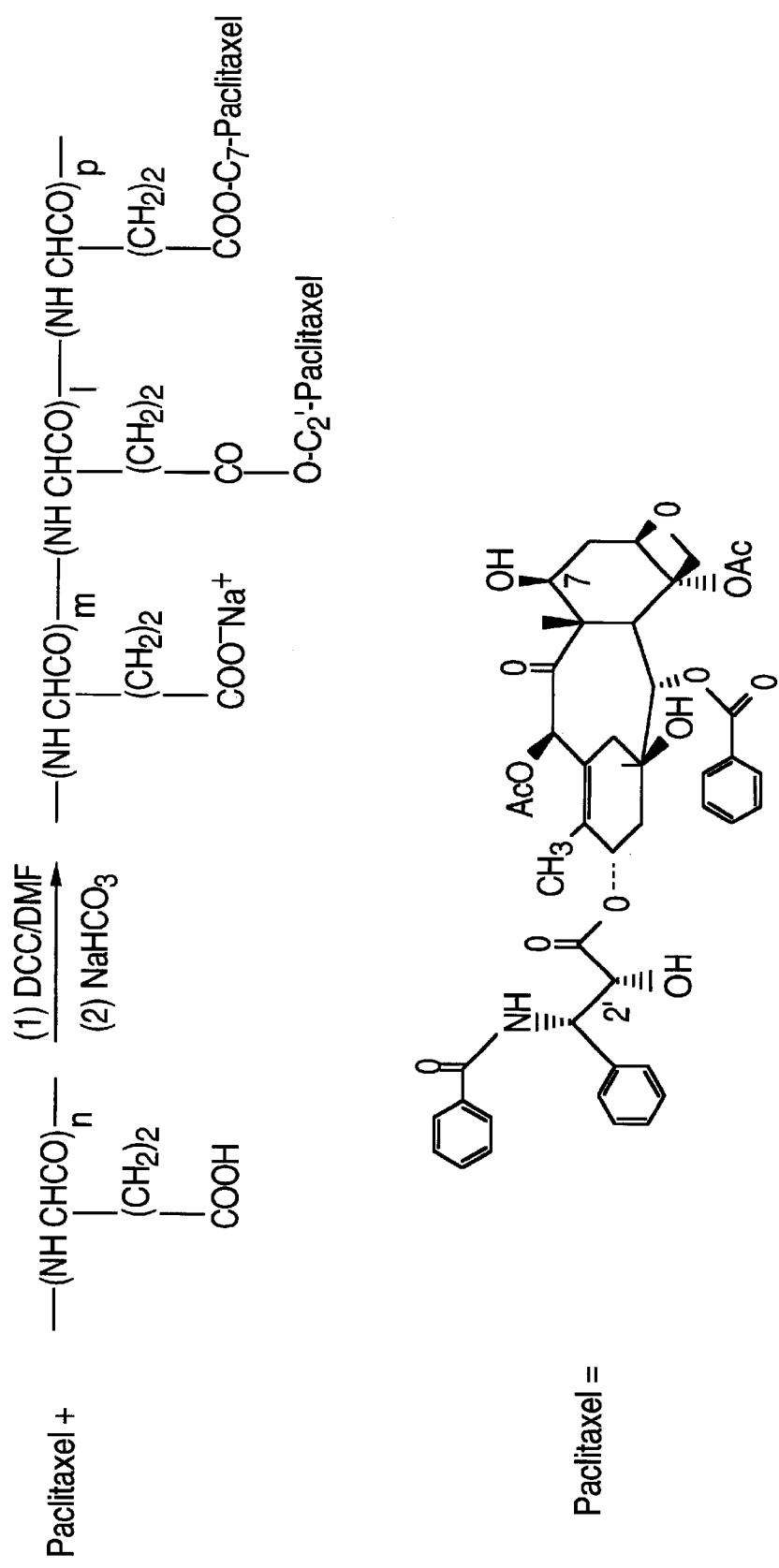
FIG. 1B shows the chemical structure and reaction scheme for production of PG-paclitaxel.

The present invention arises from the discovery of novel, water soluble formulations of paclitaxel and docetaxel, and the surprising efficacy of these formulations against tumor cells In vivo. Poly (1-glutamic acid) conjugated paclitaxel (PG-paclitaxel) administered to mice bearing ovarian carcinoma (OCa-I) caused significant tumor growth delay as compared to the same dose of paclitaxel without PG. Mice treated with paclitaxel alone or with a combination of free paclitaxel and PG showed delayed tumor growth initially, but tumors regrew to levels comparable to an untreated control group after ten days. Moreover, at the maximal tolerated dose (MTD) of the PG-paclitaxel conjugate, (160 mg equiv. paclitaxel/kg), the growth of tumors was completely suppressed, the tumors shrank, and mice observed for two months following treatment remained tumor free (MTD: defined as the maximal dose that produced 15% or less body weight loss within two weeks after a single i.v. injection). In a parallel study, the antitumor activity of PG-paclitaxel in rats with rat mammary adenocarcinoma (13762F) was examined. Again, complete tumor eradication at 40–60 mg equiv. paclitaxel/kg of PG-paclitaxel was observed. These surprising results demonstrate that the polymer-drug conjugate, PG-paclitaxel, successfully eradicates well established solid tumors in both mice and rats after a single intravenous injection. Moreover, with a half-life of 40 days at pH 7.4, PG-paclitaxel is one of the most stable water-soluble paclitaxel derivatives known (Deutsch, et al., 1989; Mathew et al., 1992; Zhao and Kingston, 1991).

DTPA-paclitaxel is also shown herein to be as effective as paclitaxel in an in vitro antitumor potency assay using a B16 melanoma cell line. DTPA-paclitaxel did not show any significant difference in antitumor effect as compared to paclitaxel against an MCa-4 mammary tumor at a dose of 40 mg/kg body weight in a single injection. Furthermore, $^{111}$Indium labeled DTPA-paclitaxel was shown to accumulate in the MCa-4 tumor as demonstrated by gamma-scintigraphy, demonstrating that the chelator conjugated anti-tumor drugs of the present invention are useful and effective for tumor imaging.

The novel compounds and methods of the present invention provide significant advances over prior methods and compositions, as the water-soluble paclitaxels are projected to improve the efficacy of paclitaxel-based anti-cancer therapy, by providing water soluble and controlled release paclitaxel derived compositions. Such compositions eliminate the need for solvents that are associated with side effects seen with prior paclitaxel compositions. In addition, radiolabeled paclitaxel, which is shown to retain anti-tumor activity, will also be useful in the imaging of tumors. Further, the present invention allows one to determine whether a paclitaxel will be taken up by a particular tumor by scintigraphy, single photon emission computer tomography (SPECT) or positron emission tomography (PET). This determination may then be used to decide the efficacy of anti-cancer treatment. This information may be helpful in guiding the practitioner in the selection of patients to undergo paclitaxel therapy.

The paclitaxel may be rendered water-soluble in two ways: by conjugating paclitaxel to water-soluble polymers which serve as drug carriers, and by derivatizing the anti-tumor drug with water soluble chelating agents. The latter approach also provides an opportunity for labeling with radionuclides (e.g., $^{111}$In, $^{90}$Y, $^{166}$Ho, $^{68}$G, $^{99m}$Tc) for nuclear imaging and/or for radiotherapy studies. The structures of paclitaxel, polyethylene glycol-paclitaxel (PEG-paclitaxel), polyglutamic acid-paclitaxel conjugate (PG-paclitaxel) and diethylenetriaminepentaacetic acid-paclitaxel (DTPA-paclitaxel) are shown in FIG. 1.

In certain embodiments of the present invention, DTPA-paclitaxel or other paclitaxel-chelating agent conjugates, such as EDTA-paclitaxel, DTTP-paclitaxel, or DOTA-paclitaxel, for example, may be prepared in the form of water-soluble salts (sodium salt, potassium salt, tetrabutylammonium salt, calcium salt, ferric salt, etc.). These salts will be useful as therapeutic agents for tumor treatment. Secondly, DTPA-paclitaxel or other paclitaxel-chelating agents will be useful as diagnostic agents which, when labeled with radionuclides such as $^{111}$In or $^{99m}$Tc, may be used as radiotracers to detect certain tumors in combination with nuclear imaging techniques. It is understood that in addition to paclitaxel (taxol) and docetaxel (taxotere), other taxane derivatives may be adapted for use in the compositions and methods of the present invention and that all such compositions and methods would be encompassed by the appended claims.

Toxicity studies, pharmacokinetics and tissue distribution of DTPA-paclitaxel have shown that in mice the $LD_{50}$ (50% lethal dose) of DPTA-paclitaxel observed with a single dose intravenous (iv) injection is about 110 mg/kg body weight. Direct comparison with paclitaxel is difficult to make because of the dose-volume restraints imposed by limited solubility of paclitaxel and vehicle toxicity associated with iv administration. However, in light of the present disclosure, one skilled in the art of chemotherapy would determine the effective and maximal tolerated dosages in a clinical study for use in human subjects.

In certain embodiments of the invention, a stent coated with the polymer-paclitaxel conjugates may be used to prevent restenosis, the closure of arteries following balloon angioplasty. Recent results in clinical trials using balloon-expandable stents in coronary angioplasty have shown a significant benefit in patency and the reduction of restenosis compared to standard balloon angioplasty (Serruys et al., 1994). According to the response-to-injury hypothesis, neointima formation is associated with increased cell proliferation. Currently, popular opinion holds that the critical process leading to vascular lesions in both spontaneous and accelerated atherosclerosis is smooth muscle cell (SMC) proliferation (Phillips-Hughes and Kandarpa, 1996). Since SMC phenotypic proliferation after arterial injury mimics that of neoplastic cells, it is possible that anti-cancer drugs may be useful to prevent neointimal SMC accumulation. Stents coated with polymer-linked anti-proliferative agents that are capable of releasing these agents over a prolonged period of time with sufficient concentration will thus prevent ingrowth of hyperplastic intima and media into the lumen thereby reducing restenosis.

Because paclitaxel has been shown to suppress collagen induced arthritis in a mouse model (Oliver et al. 1994), the formulations of the present invention are also contemplated to be useful in the treatment of autoimmune and/or inflammatory diseases such as rheumatoid arthritis. Paclitaxel binding to tubulin shifts the equilibrium to stable microtubule polymers and makes this drug a strong inhibitor of eukaryotic cell replication by blocking cells in the late G2 mitotic stage. Several mechanisms may be involved in arthritis suppression by paclitaxel. For example, paclitaxel's phase specific cytotoxic effects may affect rapidly proliferating inflammatory cells, and furthermore paclitaxel inhibits, cell mitosis, migration, chemotaxis, intracellular transport and neutrophil $H_2O_2$ production. In addition, paclitaxel may have antiangiogenic activity by blocking coordinated endothelial cell migration (Oliver et al. 1994). Therefore, the polymer conjugated prodrugs of the present invention are contemplated to be as useful as free paclitaxel in the treatment of rheumatoid arthritis. The polymer conjugated fonnulation disclosed herein would also offer the advantages of delayed or sustained release of the drug and greater solubility. It is also an aspect of the treatment of arthritis that the formulations may be injected or implanted directly into the affected joint areas.

The pharmaceutical preparations of paclitaxel or docetaxel suitable for injectable use include sterile aqueous solutions or dispersions and sterile powders for the preparation of sterile injectable solutions or dispersions. In all cases the form must be sterile and must be fluid for injection. It must be stable under the conditions of manufacture and storage and must be preserved against the contaminating action of microorganisms, such as bacteria and fungi. The carrier may be a solvent or dispersion medium containing, for example, water, ethanol, polyol (for example, glycerol, propylene glycol, and liquid polyethylene glycol, and the like), suitable mixtures thereof, and vegetable oils. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents and isotonic agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" also refers to molecular entities and compositions that do not produce an allergic or similar untoward reaction when administered to an animal or a human.

For parenteral administration in an aqueous solution, for example, the solution should be suitably buffered if necessary and the liquid diluent first rendered isotonic with sufficient saline or glucose. These particular aqueous solutions are especially suitable for intravenous and intraperitoneal administration. In this connection, sterile aqueous media which can be employed will be known to those of skill in the art in light of the present disclosure.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

DTPA-Paclitaxel

Synthesis of DTPA-Paclitaxel:

To a solution of paclitaxel (100 mg, 0.117 mmol) in dry DMF (2.2 ml) was added diethylenetriaminepentaacetic acid anhydride (DTPA A) (210 mg, 0.585 mmol) at 0° C. The reaction mixture was stirred at 4° C. overnight. The suspension was filtered (0.2 μm Millipore filter) to remove unreacted DTPA anhydride. The filtrate was poured into distilled water, stirred at 4° C. for 20 min, and the precipitate collected. The crude product was purified by preparative TLC over $C_{18}$ silica gel plates and developed in acetonitrile/water (1:1). Paclitaxel had an $R_f$ value of 0.34. The band above the paclitaxel with an $R_f$ value of 0.65 to 0.75 was removed by scraping and eluted with an acetonitrile/water (1:1) mixture, and the solvent was removed to give 15 mg of DTPA-paclitaxel as product (yield 10.4%): mp: >226° C. dec. The UV spectrum (sodium salt in water) showed maximal absorption at 228 nm which is also characteristic for paclitaxel. Mass spectrum: (FAB) m/e 1229 $(M+H)^+$, 1251 (M+Na), 1267 (M+K). In the $^1H$ NMR spectrum (DMSO-$d_6$) the resonance of $NCH_2CH_2N$ and $CH_2COOH$ of DTPA appeared as a complex series of signals at δ 2.71–2.96 ppm, and as a multiplet at δ 3.42 ppm, respectively. The resonance of C7-H at 4.10 ppm in paclitaxel shifted to 5.51 ppm, suggesting esterification at the 7-position. The rest of the spectrum was consistent with the structure of paclitaxel.

The sodium salt of DTPA-paclitaxel was also obtained by adding a solution of DTPA-paclitaxel in ethanol into an equivalent amount of 0.05 M $NaHCO_3$, followed by lyophilizing to yield a water-soluble solid powder (solubility>20 mg equivalent paclitaxel/ml).

Hydrolytic Stability of DTPA-Paclitaxel:

The hydrolytic stability of DTPA-paclitaxel was studied under accelerated conditions. Briefly, 1 mg of DTPA-paclitaxel was dissolved in 1 ml 0.5 M $NaHCO_3$ aqueous solution (pH 9.3) and analyzed by HPLC. The HPLC system consisted of a Waters 150×3.9 (i.d.) mm Nova-Pak column filled with C18 4 μm silica gel, a Perkin-Elmer isocratic LC pump, a PE Nelson 900 series interface, a Spectra-Physics UV/Vis detector and a data station. The eluant (acetonitrile/methanol/0.02M ammonium acetate=4:1:5) was run at 1.0 ml/min with UV detection at 228 nm. The retention times of DTPA-paclitaxel and paclitaxel were 1.38 and 8.83 min, respectively. Peak areas were quantitated and compared with standard curves to determine the DTPA-paclitaxel and paclitaxel concentrations. The estimated half-life of DTPA-paclitaxel in 0.5 M $NaHCO_3$ solution is about 16 days at room temperature.

Effects of DTPA-Paclitaxel on the Growth of B16 Mouse Melanoma Cells in Vitro:

Cells were seeded in 24-well plates at a concentration of $2.5 \times 10^4$ cells/ml and grown in a 50:50 Dulbecco's modified minimal essential medium (DEM) and F12 medium containing 10% bovine calf serum at 37° C. for 24 hrs in a 97% humidified atmosphere of 5.5% $CO_2$. The medium was then replaced with fresh medium containing paclitaxel or DTPA-paclitaxel in concentration ranging from $5 \times 10^{-9}$ M to $75 \times 10^{-9}$ M. After 40 hrs, the cells were released by trypsinization and counted in a Coulter counter. The final concentrations of DMSO (used to dissolve paclitaxel) and 0.05 M sodium bicarbonate solution (used to dissolve DTPA-paclitaxel) in the cell medium were less than 0.01%. This amount of solvent did not have any effect on cell growth as determined by control studies.

Figure 2:
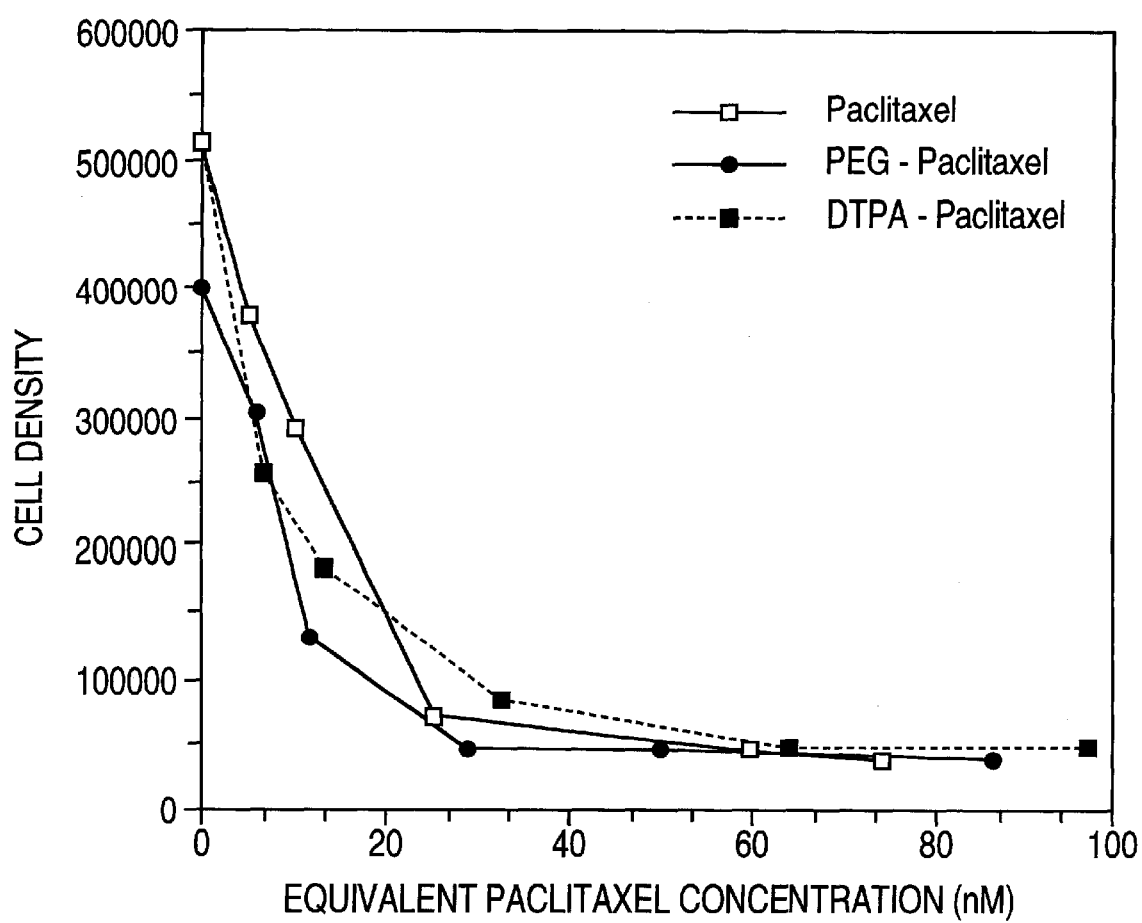
FIG. 2 shows the effect of paclitaxel, PEG-paclitaxel and DTPA-paclitaxel on proliferation of B16 melanoma cells.

The effects of DTPA-paclitaxel on the growth of B16 melanoma cells are presented in FIG. 2. After a 40-h incubation with various concentrations, DTPA-paclitaxel and paclitaxel were compared as to cytotoxicity. The $IC_{50}$ for paclitaxel and DTPA-paclitaxel are 15 nM and 7.5 nM, respectively.

Antitumor Effect on Mammary Carcinoma (MCa-4) Tumor Model:

Female C3Hf/Kam mice were inoculated with mammary carcinoma (MCa-4) in the muscles of the right thigh ($5 \times 10^5$ cells/mouse). When the tumors had grown to 8 mm (approx. 2 wks), a single dose of paclitaxel or DTPA-paclitaxel was given at 10, 20 and 40 mg equivalent paclitaxel/kg body weight. In control studies, saline and absolute alcohol/Cremophor 50/50 diluted with saline (1:4) were used. Tumor growth was determined daily, by measuring three orthogonal tumor diameters. When the tumor size reached 12 mm in diameter, the tumor growth delay was calculated. The mice were sacrificed when tumors were approximately 15 mm.

The tumor growth curve is shown in FIG. 3. Compared to controls, both paclitaxel and DTPA-paclitaxel showed antitumor effect at a dose of 40 mg/kg. The data were also analyzed to determine the mean number of days for the tumor to reach 12 mm in diameter. Statistical analysis showed that DTPA-paclitaxel delayed tumor growth significantly compared to the saline treated control at a dose of 40 mg/kg (p <0.01). The mean time for the tumor to reach 12 mm in diameter was 12.1 days for DTPA-paclitaxel compared to 9.4 days for paclitaxel (FIG. 4).

Radiolabeling of DTPA-Paclitaxel with $^{111}$In

Into a 2-ml V-vial were added successively 40 μl 0.6 M sodium acetate (pH 5.3) buffer, 40 μl 0.06 M sodium citrate buffer (pH 5.5), 20 μl DTPA-paclitaxel solution in ethanol (2% w/v) and 20 μl $^{111}InCl_3$ solution (1.0 mCi) in sodium acetate buffer (pH 5.5). After an incubation period of 30 min at room temperature, the labeled $^{111}$In-DTPA-paclitaxel was purified by passing the mixture through a C18 Sep-Pac cartridge using saline and subsequently ethanol as the mobile phase. Free $^{111}$In-DTPA (<3%) was removed by saline, while $^{111}$In-DTPA-paclitaxel was collected in the ethanol wash. The ethanol was evaporated under nitrogen gas and the labeled product was reconstituted in saline. Radiochemical yield: 84%.

Analysis of $^{111}$In-DTPA-Paclitaxel:

HPLC was used to analyze the reaction mixture and purity of $^{111}$In-DTPA-paclitaxel. The system consisted of a LDC binary pump, a 100×8.0 mm (i.d.) Waters column filled with ODS 5 μm silica gel. The column was eluted at a flow rate of 1 ml/min with a gradient mixture of water and methanol (gradient from 0% to 85% methanol over 15 min). The gradient system was monitored with a NaI crystal detector and a Spectra-Physics UV/Vis detector. As evidenced by HPLC analysis, purification by Sep-Pak cartridge removed most of the $^{111}$In-DTPA, which had a retention time of 2.7 min. The $^{111}$In-DTPA was probably derived from traces of DTPA contaminant in the DTPA-paclitaxel. A radiochromatogram of $^{111}$In-DTPA-paclitaxel correlated with its UV chromatogram, indicating that the peak at 12.3 min was indeed the target compound. Under the same chromatographic conditions, paclitaxel had a retention time of 17.1 min. The radiochemical purity of the final preparation was 90% as determined by HPLC analysis.

Figure 5:
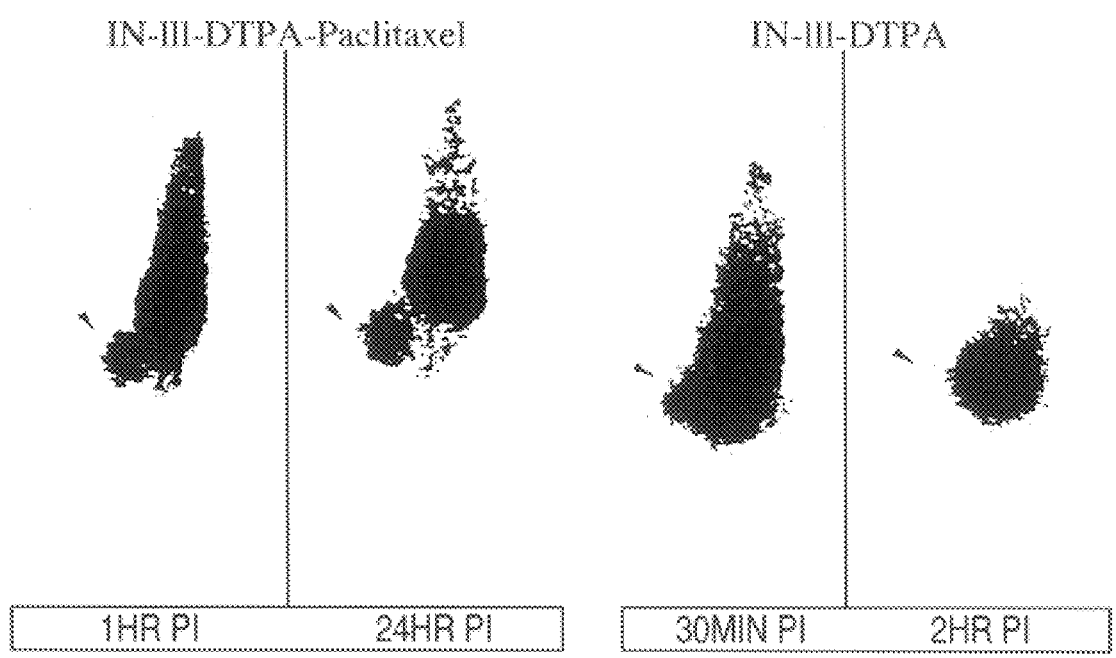
FIG. 5 shows the gamma-scintigraphs of mice bearing MCa-4 tumors following intravenous injection of $^{111}$In-DTPA-paclitaxel and $^{111}$In-DTPA. Arrow indicates the tumor.

Whole-body Scintigraphy:

Female C3Hf/Kam mice were inoculated with mammary carcinoma (MCa-4) in the muscles of the right thigh ($5 \times 10^5$ cells). When the tumors had grown to 12 mm in diameter, the mice were divided into two groups. In group I, the mice were anesthetized by intraperitoneal injection of sodium pentobarbital, followed by $^{111}$In-DTPA-paclitaxel (100–200 mCi) via tail vein. A γ-camera equipped with a medium energy collimator was positioned over the mice (3 per group). A series of 5 min acquisitions were collected at 5, 30, 60, 120, 240 min and 24 hrs after injection. In group II, the same procedures were followed except that the mice were injected with $^{111}$In-DTPA as a control. FIG. 5 shows gamma-scintigraphs of animals injected with $^{111}$In-DTPA and $^{111}$In-DTPA-paclitaxel. $^{111}$In-DTPA was characterized by rapid clearance from the plasma, rapid and high excretion in the urine with minimal retention in the kidney and negligible retention in the tumor, the liver, the intestine and other organs or body parts. In contrast, $^{111}$In-DTPA-paclitaxel exhibited a pharmacological profile resembling that of paclitaxel (Eiseman et al., 1994). Radioactivity in the brain was negligible. Liver and kidney had the greatest tissue:plasma ratios. Hepatobiliary excretion of radiolabeled DTPA-paclitaxel or its metabolites was one of the major routes for the clearance of the drug from the blood. Unlike paclitaxel, a significant amount of $^{111}$In-DTPA-paclitaxel was also excreted through kidney, which only played a minor role in the clearance of paclitaxel. The tumor had significant uptake of $^{111}$In-DTPA-paclitaxel. These results demonstrate that $^{111}$In-DTPA-paclitaxel is able to detect certain tumors and to quantify the uptake of $^{111}$In-DTPA-paclitaxel in the tumors, which in turn, may assist in the selection of patients for the paclitaxel treatment.

EXAMPLE 2

Polyglutamic Acid-Paclitaxel

The present example demonstrates the conjugation of paclitaxel to a water-soluble polymer, poly (1-glutamic acid) (PG). The potential of water-soluble polymers used as drug carriers is well established (Kopecek, 1990; Maeda and Matsumura, 1989). In addition to its ability to solubilize otherwise insoluble drugs, the drug-polymer conjugate also acts as a slow-release depot for controlled drug release.

Synthesis of PG-Paclitaxel

PG was selected as a carrier for paclitaxel because it can be readily degraded by lysosomal enzymes, is stable in plasma and contains sufficient functional groups for drug attachment. Several antitumor drugs, including Adriamycin (Van Heeswijk et al., 1985; Hoes et al., 1985), cyclophosphamide (Hirano et al., 1979), and Ara-C (Kato et al., 1984) have been conjugated to PG.

PG sodium salt (MW 34 K, Sigma, 0.35 g) was dissolved in water. The pH of the aqueous solution was adjusted to 2 using 0.2 M HCl. The precipitate was collected, dialyzed against distilled water, and lyophilized to yield 0.29 g PG.

To a solution of PG (75 mg, repeating unit FW 170, 0.44 mmol) in dry DMF (1.5 mL) was added 20 mg paclitaxel (0.023 mmol, molar ratio PG/paclitaxel=19), 15 mg dicyclohexylcarbodiimide (DCC) (0.073 mmol) and a trace amount of dimethylaminopyridine (DMAP). The reaction was allowed to proceed at room temperature for 4 hrs. Thin layer chromatography (TLC, silica) showed complete conversion of paclitaxel (Rf=0.55) to polymer conjugate (Rf=0, mobile phase, CHCl$_3$/MeOH=10:1). The reaction mixture was poured into chloroform. The resulting precipitate was collected and dried in a vacuum to yield 65 mg polymer-drug conjugate. By changing the weight ratio of paclitaxel to PG in the starting materials, polymeric conjugates of various paclitaxel concentrations can be synthesized.

The sodium salt of PG-paclitaxel conjugate was obtained by dissolving the product in 0.5 M NaHCO$_3$. The aqueous solution of PG-paclitaxel was dialyzed against distilled water (MWCO 1,000) to remove low molecular weight contaminants and excess NaHCO$_3$ salt. Lyophilization of the dialysate yielded 88.6 mg of white powder. The paclitaxel content in this polymeric conjugate was determined by UV (described below) as 21% (w/w). Yield (conversion to polymer bound paclitaxel, UV): 93%. PG-paclitaxel with higher paclitaxel content (up to 35%) can be synthesized by this method by simply increasing the ratio of paclitaxel to PG used.

$^1$H-NMR (GE model GN 500 spectrometer, 500 MHz, in D$_2$O): δ=7.75 to 7.36 ppm (aromatic components of paclitaxel); δ=6.38 ppm (C$_{10}$—H), 5.97 ppm (C$_{13}$—H), 5.63 and 4.78 ppm (C$_2$'—H), 5.55–5.36 ppm (C$_3$'—H and C$_2$—H, m), 5.10 ppm (C$_5$—H), 4.39 ppm (C$_7$—H), 4.10 (C$_{20}$—H), 1.97 ppm (OCOCH$_3$), and 1.18–1.20 ppm (C—CH$_3$) are assigned to aliphatic components of paclitaxel. Other resonances of paclitaxel were obscured by the resonances of PG. PG resonances at 4.27 ppm (H-α), 2.21 ppm (H-γ), and 2.04 ppm (H-β) are in accordance with pure PG spectrum. The couplings of polymer conjugated paclitaxel are too poorly resolved to be measured with sufficient accuracy. The solubility in water was >20 mg paclitaxel/ml.

Characterization of PG-Paclitaxel

Ultraviolet spectra (UV) were obtained on a Beckman DU-640 spectrophotometer (Fullerton, Calif.). The content of paclitaxel conjugated to PG was estimated by UV based on a standard curve generated with known concentrations of paclitaxel in methanol (λ=228 nm), assuming that the polymer conjugate in water and the free drug in methanol had the same molar extinction coefficients and that both followed Lambert Beer's law. As shown by its UV spectrum, PG-paclitaxel has characteristic paclitaxel absorption with λ shifts from 228 to 230 nm. The concentration of paclitaxel in PG-paclitaxel was estimated based on standard curve generated with known concentrations of paclitaxel in methanol at absorption of 228 rnm, assuming that the polymer conjugate in water at 230 nm and the free drug in methanol at 228 nm have the same molar extinction and both follow Lambert Beer's law.

Gel Permeation Chromatography Studies of PG-Paclitaxel

The relative molecular weight of PG-paclitaxel was characterized by gel permeation chromatography (GPC). The GPC system consisted of two LDC model III pumps coupled with LDC gradient master, a PL gel GPC column, and a Waters 990 photodiode array detector. The elutant (DMF) was run at 1.0 ml/min with UV detection set at 270 mn. Conjugation of paclitaxel to PG resulted in an increase in the molecular weight of PG-paclitaxel, as indicated by the shift of retention time from 6.4 min of PG to 5.0 min of PG-paclitaxel conjugate as analyzed by GPC. The calculated molecular weight of PG-paclitaxel containing 15–25% paclitaxel (w/w) is in the range of 45–55 kDa. The crude product contained a small molecular weight contaminant (retention time 8.0 to 10.0 min, and 11.3 min), which can be effectively removed by converting PG-paclitaxel to its sodium salt, followed by dialysis.

Hydrolytic Degradation of PG-Paclitaxel Conjugate

Figure 6:
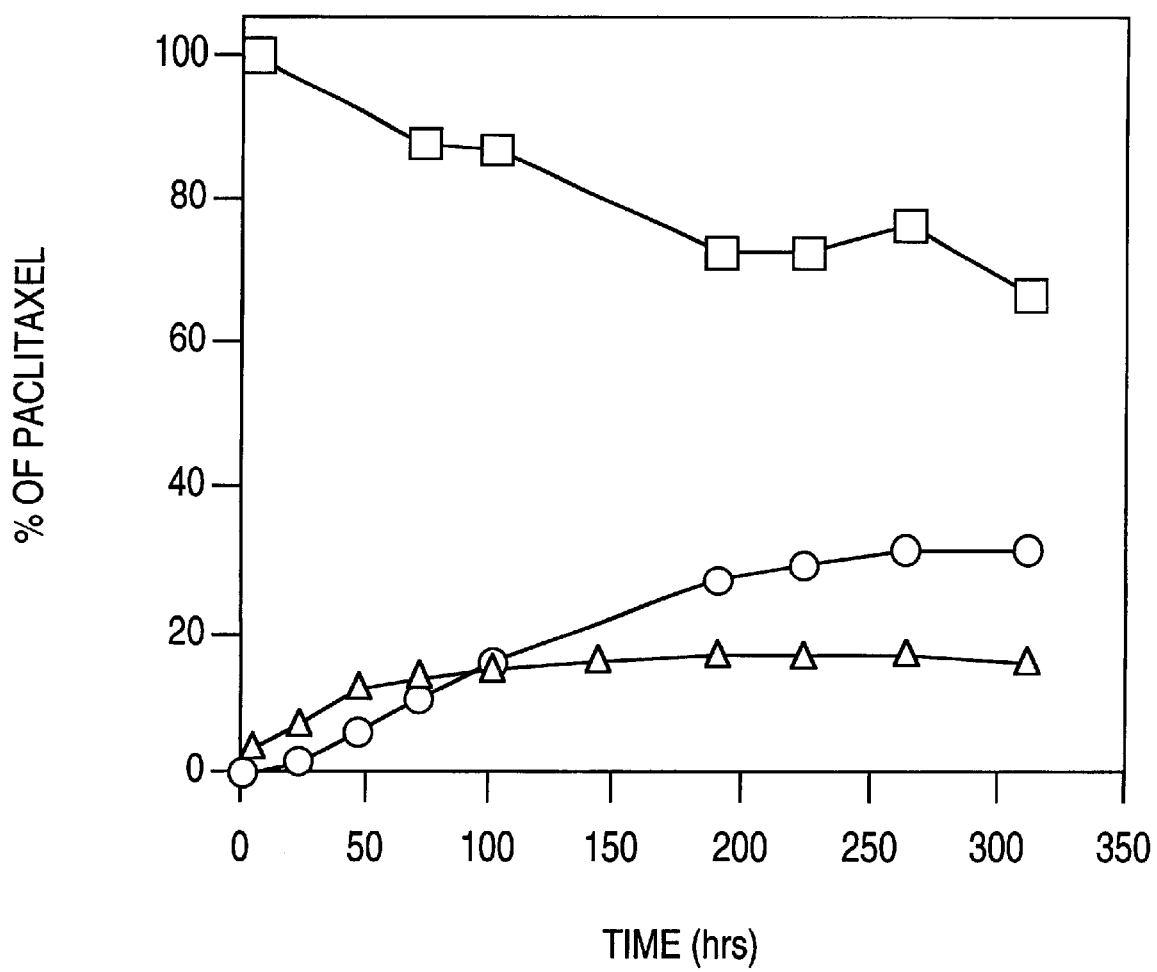
FIG. 6 shows the hydrolytic degradation of PG-paclitaxel as determined in PBS at pH 7.4 at 37 C. --□-- represents percent paclitaxel remaining attached to soluble PG, --Δ-- represents percent paclitaxel released, --○-- represents percent metabolite-1 produced.
Figure 7A:
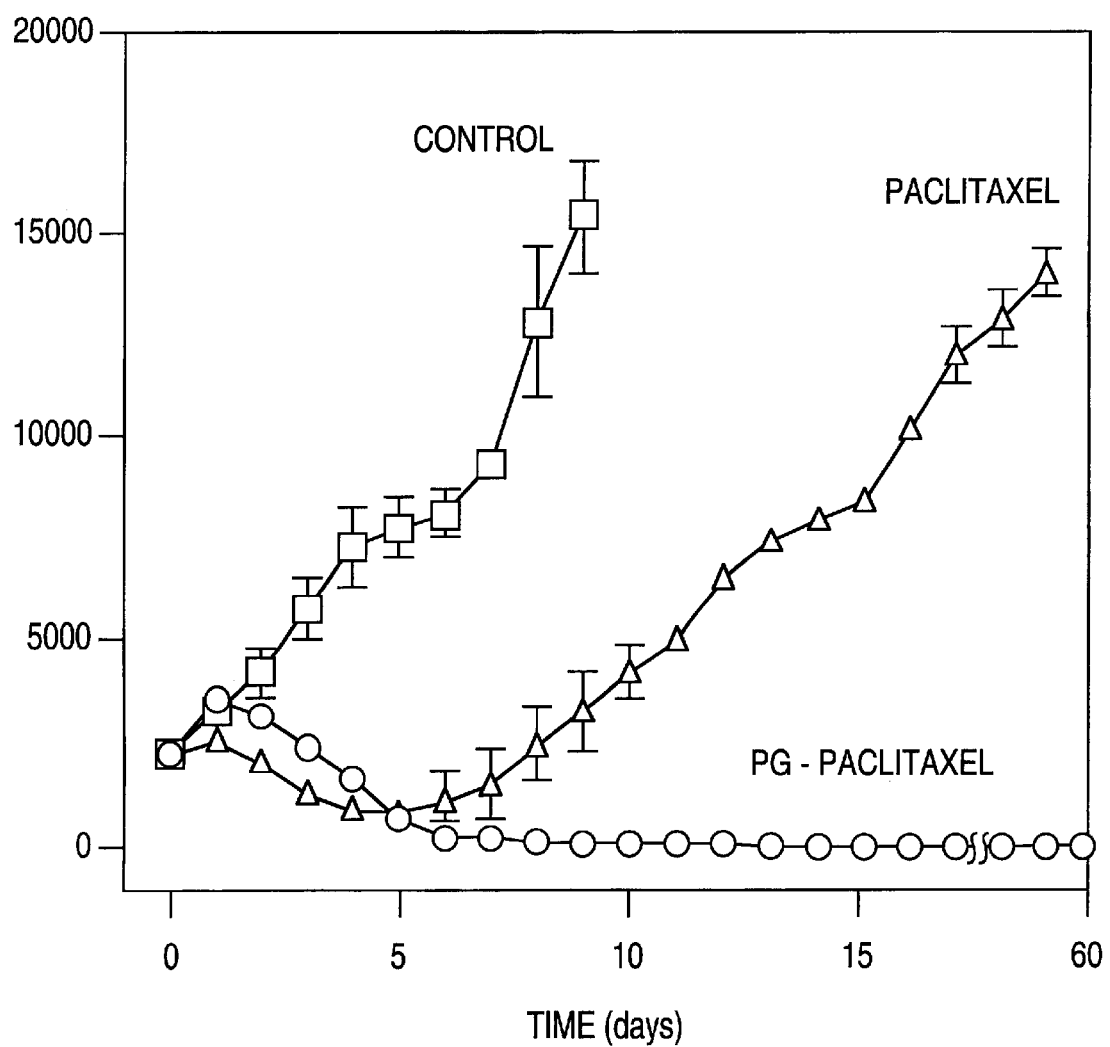
FIG. 7A shows the antitumor effect of PG-paclitaxel on rats bearing murine breast tumor (13762F). -□- represents the response to a single i.v. dose of PG (0.3 g/kg); -Δ- represents response to paclitaxel (40 mg/kg), -○- represents response to PG-paclitaxel (60 mg equiv. paclitaxel/kg).
Figure 7B:
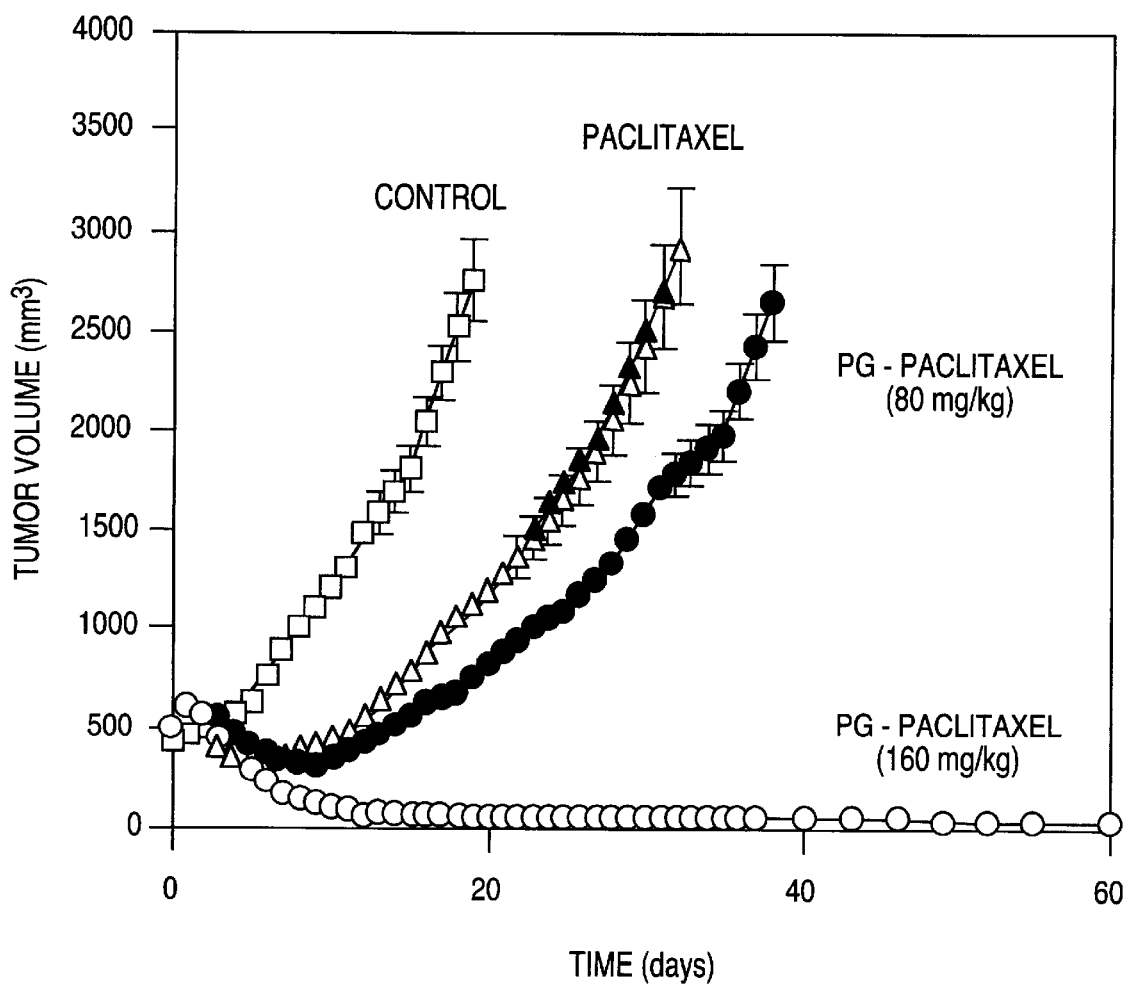
FIG. 7B shows the antitumor effect of PG-paclitaxel and paclitaxel on mice bearing OCa-1 tumors. -□- represents the response to a single i.v. dose of PG (0.8 g/kg); -Δ- represents response to paclitaxel (80 mg/kg), -●- represents response to PG-paclitaxel (80 mg equiv. paclitaxel/kg), -○- represents response to PG-paclitaxel (160 mg equiv. paclitaxel/kg).
Figure 7C:
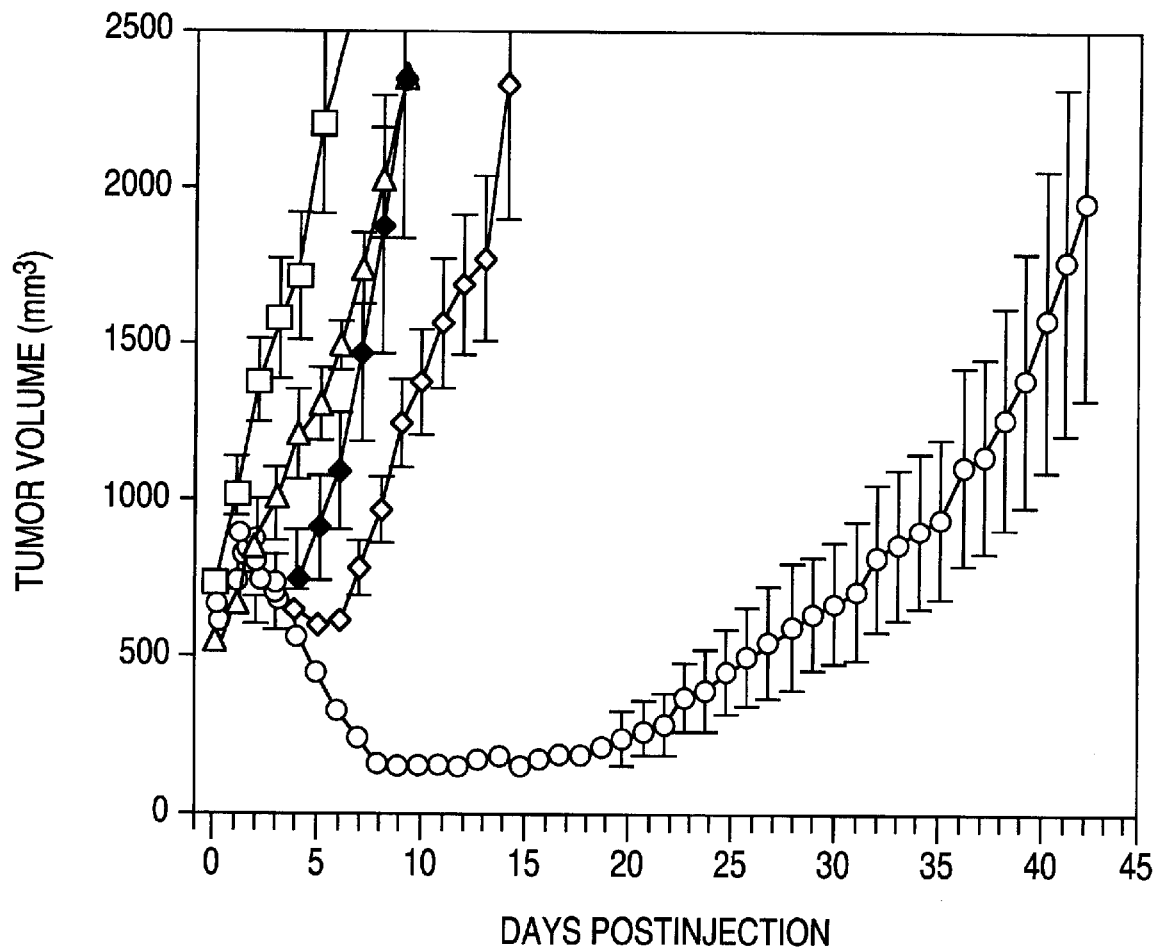
FIG. 7C shows the antitumor effect of PG-paclitaxel on mice bearing MCa-4 mammary carcinoma tumors. -□- represents the response to a single i.v. dose of saline, -Δ- represents the response to a single i.v. dose of PG (0.6 g/kg); -♦- represents response to PG-paclitaxel (40 mg/kg), -◇- represents response to PG-paclitaxel (60 mg equiv. paclitaxel/kg), -○- represents response to PG-paclitaxel (120 mg/kg).
Figure 7D:
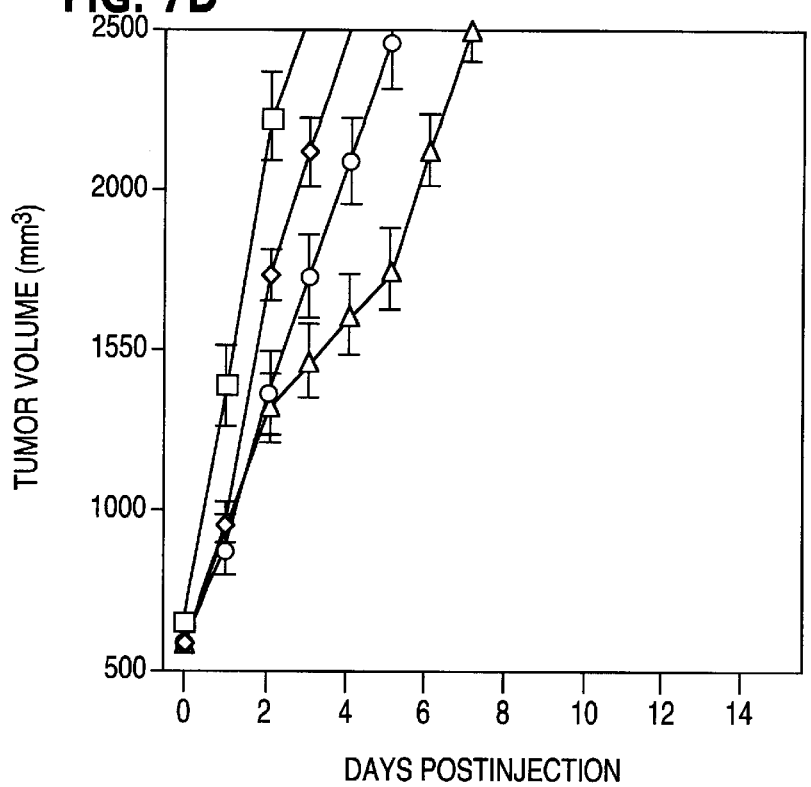
FIG. 7D shows the antitumor effect of PG-paclitaxel against soft-tissue sarcoma tumor (FSa-II) in mice. -□- represents the response to a single i.v. dose of saline, -◇- represents the response to a single i.v. dose of PG (0.8 g/kg); -○- represents response to paclitaxel (80 mg/kg), -Δ- represents response to PG-paclitaxel (160 mg equiv. paclitaxel/kg).
Figure 7E:
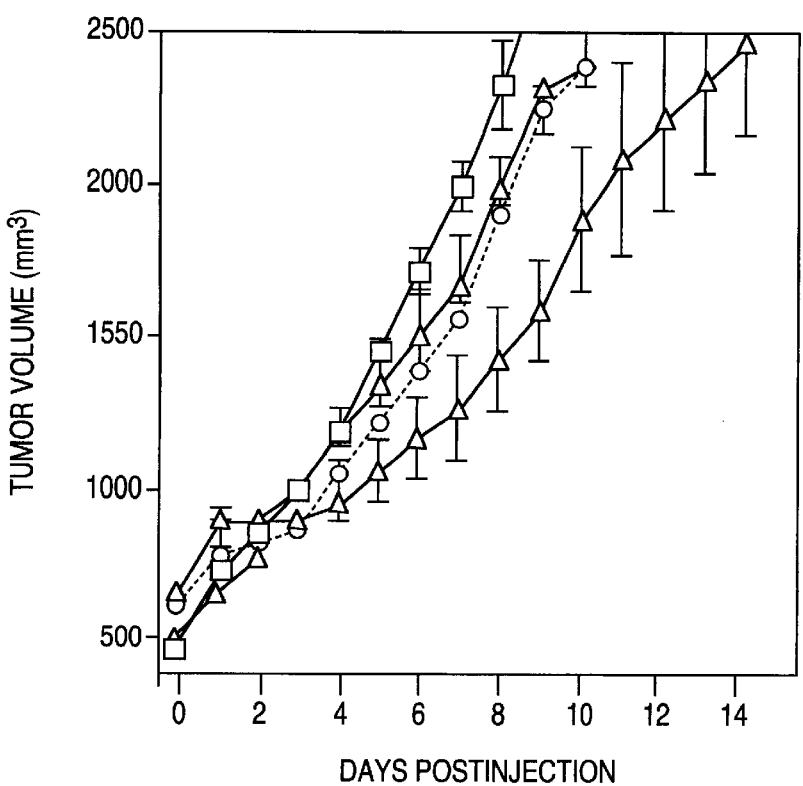
FIG. 7E shows the antitumor effect of PG-paclitaxel against syngeneic hepatocarcinoma tumor (HCa-I) in mice. -□- represents the response to a single i.v. dose of saline, -Δ- represents the response to a single i.v. dose of PG (0.8 g/kg); -○- represents response to PG-paclitaxel (80 mg/kg), -Δ- represents response to PG-paclitaxel (160 mg equiv. paclitaxel/kg).

PG-paclitaxel was dissolved in phosphate-buffered solutions (PBS, 0.01 M) at pH 6.0, pH 7.4, and pH 9.6 at an equivalent paclitaxel concentration of 0.4 mM. The solutions were incubated at 37° C. with gentle shaking. At selected time intervals, aliquots (100 μl) were removed, mixed with an equal volume of methanol and analyzed by high performance liquid chromatography (HPLC). The HPLC system consisted of a reversed-phase silica column (Nova-Pac, Waters, Calif.), a mobile phase of methanol-water (2:1, v/v) delivered at a flow rate of 1.0 ml/min, and a photodiode detector. The concentration of PG bound paclitaxel, free paclitaxel and other degradation products in each sample was calculated by comparing the peak areas with a separately obtained standard curve prepared from paclitaxel, assuming that the molar extinction coefficient of each peak at 228 nm is the same as that of paclitaxel. The half-life of the conjugate, estimated to be 132, 40 and 4 days at pH 6.0, 7.4 and 9.6 respectively, were determined by a linear least-square regression analysis. HPLC analysis revealed that incubation of PG-paclitaxel in PBS solutions produced paclitaxel and several other species including one that is more hydrophobic than paclitaxel (metabolite-1). In fact, the amount of metabolite-1, which was most probably 7-epipaclitaxel, recovered in PBS at pH 7.4 surpassed that of paclitaxel after 100 hours of incubation (FIG. 6).

In Vitro Studies

Aliquots obtained from PBS solution at pH 7.4 were subjected to analysis by a tubulin polymerization assay. The tubulin assembly reaction was performed at 32° C. in PEM buffer (pH 6.9) at a tubulin (bovine brain, Cytoskeleton Inc., Boulder, Colo.) concentration of 1 mg/ml (10 $\mu$M) in the presence of testing samples (1.0 $\mu$M equiv. Paclitaxel) and 1.0 mM GTP. Tubulin polymerization was followed by measuring the absorbance of the solution at 340 nm over time. After 15 min, calcium chloride (125 mM) was added to measure $CaCl_2$-induced depolymerization of microtubules. While PG-paclitaxel freshly dissolved in PBS was inactive in producing microtubules, aliquots of PG-paclitaxel incubated for three days did result in tubulin polymerization. The microtubules formed were stable against $CaCl_2$-induced depolymerization.

The effect of PG-paclitaxel on cell growth was also examined by tetrazolium salt (MTT) assay (Mosmann, 1983). MCF-7 cells or 13762F cells were seeded at $2\times10^4$ cells/ml in a 96-well microtiter plate treated 24 hrs later with various concentrations of PG-paclitaxel, paclitaxel or PG, and incubated for an additional 72 hr. MTT solution (20 $\mu$l, 5 mg/ml) was then added to each well and incubated for 4 hr. The supernatant was aspirated, and the MTT formazan formed by metabolically viable cells was measured by a microplate fluorescence reader at a wavelength of 590 nm. Over the three day period, PG-paclitaxel inhibited tumor cell proliferation to an extent similar to that of free paclitaxel. For human breast tumor cell line MCF-7, the resultant $IC_{50}$ values were 0.59 $\mu$M for paclitaxel and 0.82 $\mu$M for PG-paclitaxel (measured in paclitaxel equivalent units). Against the 13762F cell line, sensitivity for PG-paclitaxel ($IC_{50}$=1.86 $\mu$M) was comparable to that of paclitaxel ($IC_{50}$= 6.79 $\mu$M). For both cell lines, the $IC_{50}$ of PG alone was greater than 100 $\mu$M.

In Vivo Antitumor Activity

All animal work was carried out at the animal facility at M.D. Anderson Cancer Center in accordance with institutional guidelines. C3H/Kam mice were bred and maintained in a pathogen-free facility in the Department of Experimental Radiation Oncology. Solitary tumors were produced in the muscle of the right thigh of female C3H/Kam mice (25–30g) by injecting $5\times10^5$ murine ovarian carcinoma cells (OCa-I), mammary carcinoma (MCa-4), hepatocarcinoma (HCa-I) or fibrous sarcoma (FSa-II). In a parallel study, female Fischer 344 rats (125–150 g) were injected with $1.0\times10^5$ viable 13762F tumor cells in 0.1 ml PBS. Treatments were initiated when the tumors in mice had grown to 500 $mm^3$ (10 mm in diameter), or when the tumors in rats had grown to 2400 $mm^3$ (mean diameter 17 mm). A single dose of PG-paclitaxel in saline or paclitaxel in Cremophor EL vehicle was given in doses varying from 40 to 160 mg equiv. Paclitaxel/kg body weight. In control experiments, saline, Cremophor vehicle [50/50 Cremophor/ethanol diluted with saline (1:4)], PG (MW 38K) solution in saline, and a paclitaxel/PG mixture were used. Tumor growth was determined daily (FIGS. 7A, 7B, 7C, 7D and 7E) by measuring three orthogonal tumor diameters. Tumor volume was calculated according to formula $(A\times B\times C)/2$. Absolute growth delay (AGD) in mice is defined as the time in days for tumors treated with various drugs to grow from 500 to 2,000 $mm^3$ in mice minus the time in days for tumors treated with saline control to grow from 500 to 2,000 $mm^3$. Table 1 summarizes acute toxicity of PG paclitaxel in rats in comparison with paclitaxel/Cremophor. Table 2 summarizes the data concerning the effect of PG-paclitaxel against MCa-4, FSa-II and HCa-I tumors in mice. The data are also summarized in FIG. 7A–FIG. 7E.

TABLE 1

Acute Toxicity of PG-Paclitaxel in Fischer Rats*

| Group | Dose (mg/kg) | # of Toxic Death | Body Weight Loss in % | Time at Nadir (days) | Time of Full Recovery (days) |
|---|---|---|---|---|---|
| PG-paclitaxel[a] | 60 | 1/4 | 15.7 | 7 | 14 |
| PG-paclitaxel[a] | 40 | 0/4 | 11.1 | 6 | 11 |
| Paclitaxel[b] | 60 | 1/4 | 16.7 | 6 | 15 |
| Paclitaxel[b] | 40 | 0/3 | 17.9 | 6 | 16 |
| saline | 1.0 ml | 0/2 | 5.2 | 1 | 7 |
| PG[c] | 0.3g/kg | 0/2 | 4.3 | 2 | 8 |
| Cremophor Vehicle[d] | 2.0 ml | 0/2 | 6.9 | 1 | 9 |

*Drugs were administered intravenously into 13762F tumor-bearing Fischer rats (female, 130 g) in a single injection.
[a]PG-paclitaxel solution was prepared by dissolving the conjugate in saline (8 mg equiv. paclitaxel/ml). The injected volume at 60 mg/kg was 0.975 ml per rat.
[b]Paclitaxel Cremophor solution was prepared by dissolving paclitaxel in a 1:1 mixture of ethyl alcohol and Cremophor (30 mg/ml). This stock solution was further diluted with saline (1:4) before injection. The final concentration of paclitaxel in the solution was 6 mg/ml. The injected volume at 60 mg/kg was 1.3 ml per rat.
[c]PG solution was prepared by dissolving the polymer in saline (22 mg/ml). The injected dose was 0.3 g/kg (1.8 ml per rat), which was equivalent to paclitaxel dose of 60 mg/kg.
[d]Cremophor vehicle was prepared by diluting a mixture of ethyl alcohol and cremophor (1:1) with saline (1:4).

TABLE 2

The Antitumor Effect of PG-Paclitaxel Against Different Types of In vivo Murine Tumors

| Tumor | Drug[a] | Time to Grow[bb] 500–2000 $mm^3$ | AGD[c] | t-test[d] |
|---|---|---|---|---|
| MCa-4 | Saline | 4.8 ± 0.8 (5) | — | — |
| | PG (0.6 g/kg) | 9.3 ± 1.1 (4) | 4.5 | 0.0114 |
| | Cremophor Vehicle | 6.1 ± 0.7 (5) | 1.3 | 0.265 |
| | PG-Pacl (40 mg/kg) | 8.6 ± 1.2 (4) | 3.8 | 0.026 |
| | PG-Pacl (60 mg/kg) | 14.2 ± 1.1 (5) | 9.4 | 0.0001 |
| | PG-Pacl (120 mg/kg) | 44.4 ± 2.9 (5) | 39.6 | <0.0001 |
| | Paclitaxel (40 mg/kg) | 9.0 ± 0.6 (4) | 4.2 | 0.0044 |
| | Paclitaxel (60 mg/kg) | 9.3 ± 0.3 (5) | 4.5 | 0.0006 |
| FSa-II | Saline | 1.9 ± 0.1 (5) | — | — |
| | PG (0.8 g/kg) | 2.8 ± 0.2 (6) | 0.9 | 0.0043 |
| | Cremophor Vehicle | 2.2 ± 0.2 (6) | 0.3 | 0.122 |
| | PG-Pacl (80 mg/kg) | 3.8 ± 0.4 (6) | 1.9 | 0.0016 |
| | PG-Pacl (160 mg/kg) | 5.1 ± 0.3 (13) | 3.2 | <0.0001 |
| | Paclitaxel (80 mg/kg) | 4.2 ± 0.3 (6) | 2.3 | 0.0002 |
| | PG + Paclitaxel | 3.0 ± 0.2 (6) | 1.1 | 0.0008 |

TABLE 2-continued

The Antitumor Effect of PG-Paclitaxel Against
Different Types of In vivo Murine Tumors

| Tumor | Drug[a] | Time to Grow[bb] 500–2000 mm$^3$ | AGD[c] | t-test[d] |
|---|---|---|---|---|
| HCa-I | Saline | 7.3 ± 0.3 (5) | — | — |
| | PG (0.8 g/kg) | 7.7 ± 0.4 (4) | 0.4 | 0.417 |
| | Cremophor Vehicle | 6.8 ± 0.8 (5) | −0.5 | 0.539 |
| | PG-Pacl (40 mg/kg) | 8.2 ± 0.7 (5) | 0.9 | 0.218 |
| | PG-Pacl (80 mg/kg) | 8.6 ± 0.2 (5) | 1.3 | 0.0053 |
| | PG-Pacl (160 mg/kg) | 11.0 ± 0.8 (4) | 3.7 | 0.0023 |
| | Paclitaxel (80 mg/kg) | 6.4 ± 0.5 (5) | −0.9 | 0.138 |
| | PG + Paclitaxel | 6.7 ± 0.4 (5) | −0.6 | 0.294 |

[a]Mice bearing 500 mm$^3$ tumors in the right leg were treated with various doses of PG-paclitaxel (40–120 mg equiv. paclitaxel/kg) in saline or paclitaxel in Cremophor vehicle i.v. in a single injection. Control animals were treated with saline (0.6 ml), Cremophor vehicle (0.5 ml), PG solution in saline, or PG g/kg) plus paclitaxel (80 mg/kg).
[b]Tumor growth was determined by daily measurement of three orthogonal diameters with calipers and the volume was calculated as (a × b × c)/2. Shown in brackets are the number of mice used in each group. The time in days to grow from 500 mm$^3$ to 2000 mm$^3$ are presented mean ± standard deviation.
[c]Absolute growth delay (AGD) defined as the time in days for tumors treated with various drugs to grow from 500 to 2000 mm$^3$ minus the time in days for tumors treated with saline control to grow from 500 to 2000 mm$^3$.
[d]The time in days to grow from 500 to 2000 mm$^3$ were compared for treatment groups and saline group using Student's t-Test. P-values are two-sided and were taken to be significant when less than to equal 0.05.

EXAMPLE 3

Polyethylene Glycol-Paclitaxel
Synthesis of Polyethylene Glycol-Paclitaxel (PEG-Paclitaxel)

The synthesis was accomplished in two steps. First 2'-succinyl-paclitaxel was prepared according to a reported procedure (Deutsch et al., 1989). Paclitaxel (200 mg, 0.23 mmol) and succinic anhydride (288 mg, 2.22 mmol) were allowed to react in anhydrous pyridine (6 ml) at room temperature for 3 hrs. The pyridine was then evaporated, and the residue was treated with water, stirred for 20 min, and filtered. The precipitate was dissolved in acetone, water was slowly added, and the fine crystals were collected to yield 180 mg 2'-succinyl-paclitaxel. PEG-paclitaxel was synthesized by an N-ethoxycarbonyl-2-ethoxy-1,2-dihydroquinoline (EEDQ) mediated coupling reaction. To a solution of 2'-succinyl-paclitaxel (160 mg, 0.18 mmol) and methoxypolyoxyethylene amine (PEG-NH$_2$, MW 5000, 900 mg, 0.18 mmol) in methylene chloride was added EEDQ (180 mg, 0.72 mmol). The reaction mixture was stirred at room temperature for 4 hrs. The crude product was clromatographed on silica gel with ethyl acetate followed by chloroform-methanol (10:1). This gave 350 mg of product. $^1$H NMR (CDCl$_3$) δ 2.76 (m, succinic acid, COCH$_2$CH$_2$CO$_2$), δ 3.63 (PEG, OCH$_2$CH$_2$O), δ 4.42 (C7—H) and δ 5.51 (C2'—H). Maximal UV absorption was at 288 nm which is also characteristic for paclitaxel. Attachment to PEG greatly improved the aqueous solubility of paclitaxel (>20 mg equivalent paclitaxel/ml water).

Hydrolytic Stability of PEG-Paclitaxel

Figure 8:
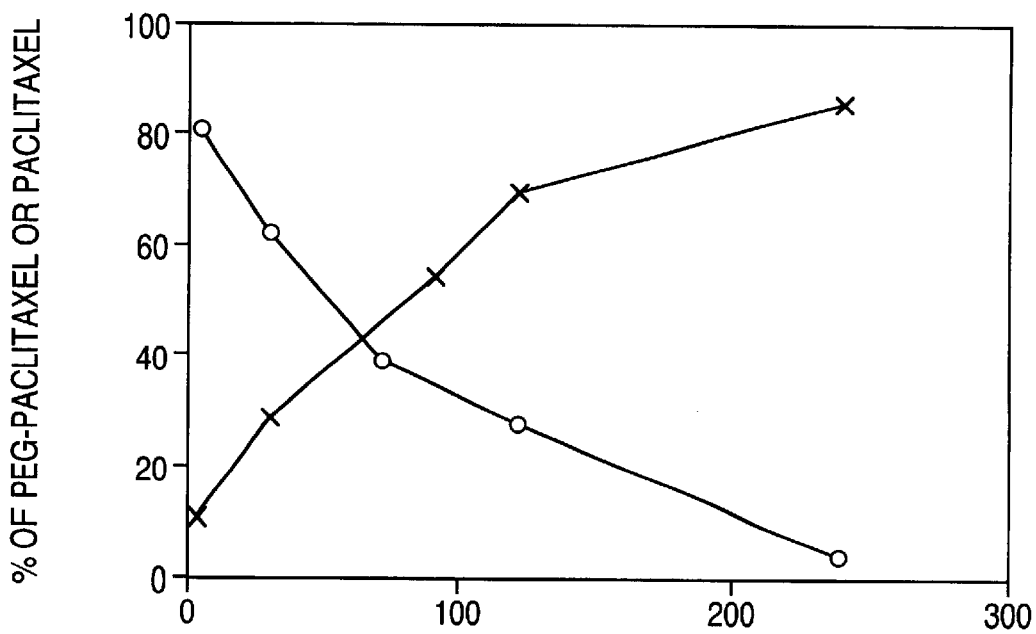
FIG. 8 shows the release profile of paclitaxel from PEG-paclitaxel in phosphate buffer (pH 7.4). Paclitaxel, -X-; PEG-paclitaxel, -○-.

PEG-Paclitaxel was dissolved in phosphate buffer (0.01M) at various pHs at a concentration of 0.4 mM and the solutions were allowed to incubate at 37° C. with gentle shaking. At selected time intervals, aliquots (200 μl) were removed and lyophilized. The resulting dry powders were redissolved in methylene chloride for gel permeation chromatography (GPC analysis). The GPC system consisted of a Perkin-Elmer PL gel mixed bed column, a Perkin-Elmer isocratic LC pump, a PE Nelson 900 series interface, a Spectra-Physics UV/Vis detector and a data station. The elutant (methylene chloride) was run at 1.0 ml/min with the WV detector set at 228 nm. The retention times of PEG-paclitaxel and paclitaxel were 6.1 and 8.2 min, respectively. Peak areas were quantified and the percentage of PEG-paclitaxel remaining and the percentage of paclitaxel released were calculated. The half life of PEG-paclitaxel determined by linear least-squares at pH 7.4 was 54 min. The half-life at pH 9.0 was 7.6 min. Release profiles of paclitaxel from PEG-paclitaxel at pH 7.4 is shown in FIG. 8.

Cytotoxicity Studies of PEG-paclitaxel Using B16 Mouse Melanoma Cells In Vitro

Following the procedure described in the cytotoxicity studies with DTPA-paclitaxel, melanoma cells were seeded in 24-well plates at a concentration of $2.5 \times 10^4$ cells/ml and grown in a 50:50 Dulbecco's modified minimal essential medium (DME) and F12 medium containing 10% bovine calf serum at 37° C. for 24 hrs in a 97% humidified atmosphere of 5.5% CO$_2$. The medium was then replaced with fresh medium containing paclitaxel or its derivatives in concentrations ranging from $5 \times 10^{-9}$ M to $75 \times 10^{-9}$ M. After 40 hrs, the cells were released by trypsinization and counted in a Coulter counter. The final concentrations of DMSO (used to dissolve paclitaxel) and 0.05 M sodium bicarbonate solution (used to dissolve PEG-paclitaxel) in the cell medium were less than 0.01%. This amount of solvent did not have any effect on cell growth as determined by control studies. Furthermore, PEG in the concentration range used to generate an equivalent paclitaxel concentration from $5 \times 10^{-9}$ M to $75 \times 10^{-9}$ M also did not effect cell proliferation.

Antitumor Effect of PEG-Paclitaxel Against MCa-4 Tumor in Mice

To evaluate the antitumor efficacy of PEG-paclitaxel against solid breast tumors, MCa-4 cells ($5 \times 10^5$ cells) were injected into the right thigh muscle of female C3Hf/Kam mice. As described in Example 1 with the DTPA-paclitaxel, when the tumors were grown to 8 mm (Approx. 2 wks), a single dose of paclitaxel or PEG-paclitaxel was given at 10, 20 and at 40 mg equivalent paclitaxel/kg body weight. Paclitaxel was initially dissolved in absolute ethanol with an equal volume of Cremophor. This stock solution was further diluted (1:4 by volume) with a sterile physiological solution within 15 minutes of injection. PEG-paclitaxel was dissolved in saline (6 mg equiv. paclitaxel/ml) and filtered thiough a sterile filter (Millipore, 4.5 μm). Saline, paclitaxel vehicle, absolute alcohol:Cremophor (1:1) diluted with saline (1:4) and PEG solution in saline (600 mg/kg body weight) were used in control experiments. Tumor growth was determined daily, by measuring three orthogonal tumor diameters. When the tumor size reached 12 mm in diameter, the tumor growth delay was calculated.

Figure 9:
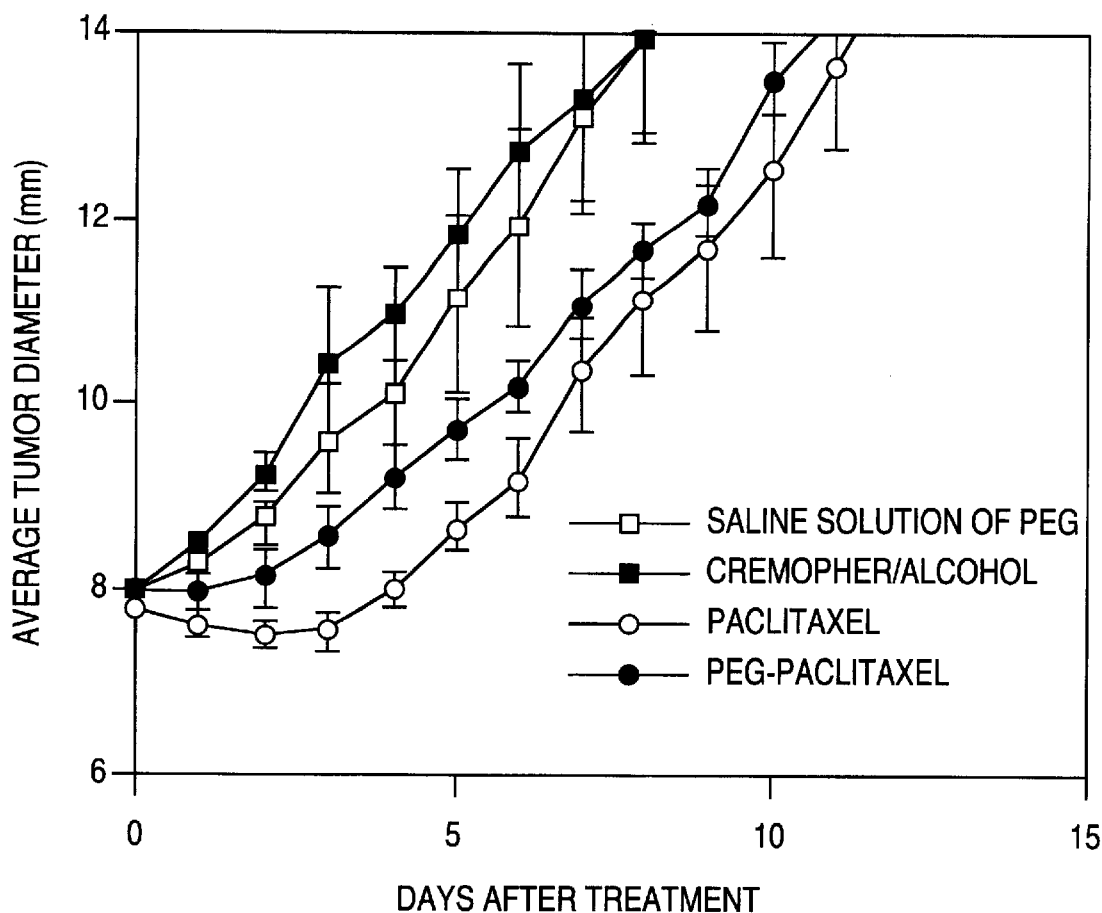
FIG. 9 shows the antitumor effect of PEG-paclitaxel on MCa-4 mammary tumors. -□- represents the response a single i.v. injection with a saline solution of PEG (60 mg/ml), -■- represents the response to the Cremophor/alcohol vehicle, -○-represents a single dose of 40 mg/kg body weight of paclitaxel, -●- represents PEG-paclitaxel at 40 mg equiv. paclitaxel/kg body weight.

The tumor growth curve is shown in FIG. 9. At a dose of 40 mg/kg, both PEG-paclitaxel and paclitaxel effectively delayed tumor growth. Paclitaxel was more effective than PEG-paclitaxel, although the difference was not statistically significant. Paclitaxel treated tumors required 9.4 days to reach 12 mm in diameter whereas PEG-paclitaxel-treated tumors required 8.5 days. Statistically, these values were significant ($p > 0.05$) as compared to their corresponding controls, which were 6.7 days for the paclitaxel vehicle and 6.5 days for the saline solution of PEG (FIG. 4).

While the compositions and methods of this invention have been described in terms of preferred embodiments, it will be apparent to those of skill in the art that variations may be applied to the compositions, methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Bartoni and Boitard, "In vitro and in vivo antitumoral activity of free, and encapsulated taxol," *J. Microencapsulation*, 7:191–197, 1990.

Cortes, J. E. and Pazdur, R., "Docetaxel", *Journal of Clinical Oncology* 13:2643–2655, 1995.

Deutsch et al., "Synthesis of congeners and prodrugs. 3. water-soluble prodrugs of taxol with potent antitumor activity," *J. Med. Chem.*, 32:788–792, 1989.

Eiseman et al., "Plasma pharmacokinetics and tissue distribution of paclitaxel in CD2F1 mice," *Cancer Chemother. Pharmacol.*, 34:465–471, 1994.

Fidler, et al., "The biology of cancer invasion and metastasis," Adv. Cancer Res., 28:149–250, 1987.

Goldspiel, "Taxol pharmaceutical issues: preparation, administration, stability, and compatibility with other medications," *Ann. Pharmacotherapy*, 28:S23–26, 1994.

Greenwald et al., "Highly water soluble Taxol derivatives, 7-polyethylene glycol esters as potential products," *J. Org. Chem.*, 60:331–336, 1995.

Greenwald et al., "Highly water soluble taxol derivative: 2'-polyethylene glycol esters as potential products", *Bioorganic & Medicinal Chemistry Letters*, 4:2465–2470, 1994.

Hirano et al., "Polymeric derivatives of activated cyclophosphamide as drug delivery systems in antitumor therapy", *Makromol. Chem.*, 180:1125–1130, 1979.

Hoes et al., "Optimization of macromolecular prodrugs of the antitumor antibiotic adriamycin", *J. Controlled Release*, 2:205–213, 1985.

Hofle et al., DE38942.

Horwitz et al., "Taxol, mechanisms of action and resistance," *J. Natl. Cancer Inst. Monographs* No. 15, pp. 55–61, 1993.

Kato et al., "Antitumor activity of 1-b-arabinofuranosylcytosine conjugated with polyglutamic acid and its derivative", *Cancer Res.*, 44:25, 1984.

Kopecek, "The potential of water-soluble polymeric carriers in targeted and site-specific drug delivery", *J. Controlled Release*, 11:279–290, 1990.

Kopecek and Kopeckova, "Targetable water-soluble polymeric anticancer drugs: achievements and unsolved problems," *Proceed. Intern Symp. Control. Rel. Bioact. Mater.*, 20:190–191, 1993.

Maeda and Matsumura, "Tumoritropic and lymphotropic principles of macromolecular drugs", *Critical Review in Therapeutic Drug Carrier Systems*, 6:193–210, 1989.

Magri and Kingston, "Modified taxols. 2. Oxidation products of taxol," *J. Org. Chem.*, 51:797–802, 1986.

Mathew et al., "Synthesis and evaluation of some water-soluble prodrugs and derivatives of taxol with antitumor activity," *J. Med. Chem.*, 35:145–151, 1992.

Mosmann, T., "Rapid colormetric assay for cellular growth and survival: application to proliferation and cytotoxic assay," *J. Immunol. Methods*, 65:55–63, 1983.

Oliver, S. J. et al., "Suppression of collagen-induced arthritis using an angiogenesis inhibitor, AGM-1470, and a microtubule stabilizer, *Taxol,*" *Cellular Immunology* 157:291–299, 1994.

Phillips-Hughes and Kandarpa, "Restenosis: pathophysiology and preventive strategies," *JVIR* 7:321–333, 1996.

Reynolds, T., "Polymers help guide cancer drugs to tumor targets- and keep them there," *J. Natl. Cancer Institute*, 87:1582–1584, 1995.

Scudiero et al. "Evaluation of a Soluble Tetrazolium/Foimazan Assay for Cell Growth and Drug Sensitivity in Culture Using Human and Other Tumor Cell Lines," *Cancer Research*, 48:4827–4833, 1988.

Serruys et al., "A comparison of balloon-expandable-stent implantation with balloon angioplasty in patients with coronary artery disease," *N. Engl. J. Med.*, 331:489–495, 1994.

Sharma and Straubinger, "Novel taxol formulations: Preparation and Characterization of taxol-containing liposomes," *Pharm. Res.* 11:889–896, 1994.

U.S. Pat. No. 5,583,153 van Heeswijk et al., "The synthesis and characterization of polypeptide-adriamycin conjugate and its complexes with adriamycin. Part 1", J. *Controlled Release*, 1:301–315, 1985.

Weiss et al., "Hypersensitivity reactions from Taxol," *J. Clin. Oncol.*, 8:1263–1268, 1990.

WO 96/25176

Zhao, Z. and Kingston, D. G. I., "Modified taxols. 6. Preparation of water-soluble taxol phosphates," *J. Nat. Prod.*, 54:1607–1611, 1991.

What is claimed is:

1. A pharmaceutical composition comprising a conjugate comprising an anti-tumor drug conjugated to a water soluble polyglutamic acid polymer, wherein said polymer has a molecular weight of about 5,000 to about 100,000 daltons, wherein said drug is conjugated to said polymer so as to provide a drug conjugate having a higher water solubility than the unconjugated drug and the ability to accumulate in a tumor, and wherein said anti-tumor drug is paclitaxel, docetaxel, etoposide, teniposide, camptothecin or epothilone.

2. The pharmaceutical composition of claim 1, wherein said antitumor drug is directly conjugated to said water soluble polyglutamic acid polymer.

3. The pharmaceutical composition of claim 1, wherein said conjugate comprises paclitaxel.

4. The pharmaceutical composition of claim 1, wherein said conjugate comprises docetaxel.

5. The pharmaceutical composition of claim 2, wherein said conjugate comprises camptothecin.

6. The pharmaceutical composition of claim 1, wherein said conjugate comprises etoposide.

7. The pharmaceutical composition of claim 1, wherein said polyglutamic acid polymer is poly (L-glutamic) acid.

8. The pharmaceutical composition of claim 1, wherein said polyglutamic acid polymer is poly (D-glutamic) acid.

9. The pharmaceutical composition of claim 3, wherein said conjugate comprises up to 35% by weight of paclitaxel.

10. The pharmaceutical composition of claim 9, wherein said conjugate comprises from about 15% to about 25% by weight of paclitaxel.

11. The pharmaceutical composition of claim 10, wherein said drug conjugate has a molecular weight in the range of from 45 kd to 55 kd.

12. A pharmaceutical composition comprising a conjugate comprising an antitumor drug conjugated to a water soluble polymer comprising a polyglutamic acid polymer, wherein said polyglutamic acid polymer has a molecular weight of about 20,000 to about 80,000 daltons, said drug conjugate comprises up to 35% by weight of drug, said drug is conjugated to said water soluble polymer so as to provide a drug conjugate having a higher water solubility than the unconjugated drug and the ability to accumulate in a tumor, and wherein said antitumor drug is paclitaxel.

13. The pharmaceutical composition of claim 12, wherein said antitumor drug is directly conjugated to said water soluble polyglutamic acid polymer.

14. A pharmaceutical composition comprising a conjugate of paclitaxel conjugated to a water soluble polymer comprising a polyglutamic acid polymer, wherein said polyglutamic acid polymer has a molecular weight of about 30,000 to about 60,000 daltons, and said conjugate comprises up to 35% by weight of paclitaxel, wherein said conjugate has a higher water solubility than unconjugated paclitaxel and the ability to accumulate in a tumor.

15. The pharmaceutical composition of claim 14, wherein said paclitaxel is directly conjugated at its 2'-hydroxyl group to said water soluble polyglutamic acid polymer.

16. The pharmaceutical composition of claim 1, wherein said conjugate comprises epothilone.

* * * * *